US009617297B2

(12) United States Patent
McDonald et al.

(10) Patent No.: US 9,617,297 B2
(45) Date of Patent: Apr. 11, 2017

(54) APOPLAST WASH FLUID RECOVERY FOR IMPROVED RECOMBINANT ENDOGLUCANASE EXTRACTION IN TABACCO LEAVES

(71) Applicant: The Regents of the University of California, Oakland, CA (US)

(72) Inventors: Karen A. McDonald, Davis, CA (US); Nathaniel J. Kingsbury, Davis, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 14/052,617

(22) Filed: Oct. 11, 2013

(65) Prior Publication Data

US 2014/0106434 A1    Apr. 17, 2014

Related U.S. Application Data

(60) Provisional application No. 61/712,774, filed on Oct. 11, 2012.

(51) Int. Cl.
*C07K 1/14* (2006.01)

(52) U.S. Cl.
CPC ........ *C07K 1/14* (2013.01); *C12Y 302/01004* (2013.01)

(58) Field of Classification Search
None
See application file for complete search history.

(56) References Cited

U.S. PATENT DOCUMENTS

| 5,558,071 A * | 9/1996 | Ward et al. .................... 123/598 |
| 6,841,659 B2 * | 1/2005 | Turpen ................. C07K 14/415 435/183 |
| 7,034,128 B2 | 4/2006 | Turpen et al. |
| 8,461,129 B2 * | 6/2013 | Bolduc et al. .................. 514/54 |
| 2011/0028412 A1 * | 2/2011 | Cappello et al. ............... 514/25 |
| 2013/0041394 A1 * | 2/2013 | Drager et al. ................. 514/394 |
| 2013/0067807 A1 * | 3/2013 | Vezina et al. ............. 47/58.1 R |
| 2013/0084243 A1 * | 4/2013 | Goetsch et al. ............ 424/1.49 |
| 2013/0096073 A1 * | 4/2013 | Sidelman ..................... 514/21.6 |

FOREIGN PATENT DOCUMENTS

WO    WO 2012/019660    *  2/2012  ............. C12N 15/82

OTHER PUBLICATIONS

Dai et al, Transgenic Research (2005) vol. 14, pp. 627-643.*
Lim et al, Starch (1999) vol. 51, pp. 120-125.*
Lohaus et al, Physiologia Plantarum (2001) vol. 111, pp. 457-465.*
Shewry and Fido, Protein Extraction from Plant Tissues, from Methods in Molecular Biology, vol. 59: Protein Purification Protocols (1996), edited by S Doonan, Humana Press Inc , Totowa, NJ.*
Marillonet et al. Systemic Agrobacterium tumefaciens-mediated transfection of viral replicaons for efficient transient expression.*
Komarnytsky et al. Production of recombinant proteins in tobacco guttation fluid. (2000) Plant Physiology; vol. 124; pp. 927-933.*
Gregory, R.P.F., "A Rapid Assay for Peroxidase Activity", Biochemical Journal, vol. 101, 1966, pp. 582-583.
Hehle et al., "Antibody Degradation in Tobacco Plants: a Predominantly Apoplastic Process", Bmc Biotechnology, vol. 11, No. 128, 2011, pp. 1-12.
Hellwig et al., "Plant Cell Cultures for the Production of Recombinant Proteins", Nature Biotechnology, vol. 22, No. 11, Nov. 2004, pp. 1415-1422.
Huang et al., "Structural Organization and Differential Expression of Rice Alpha-Amylase Genes", Accession No. M59351.1, available online at <http://www.ncbi.nlm.nih.gov/nuccore/169770/?report=genbank>, 1990, 2 pages.
Kuta et al., "Agrobacterium-Induced Hypersensitive Necrotic Reaction in Plant Cells: A Resistance Response against Agrobacterium-Mediated DNA Transfer", African Journal of Biotechnology vol. 4, No. 8, Aug. 2005, pp. 752-757.
Laymon et al., "Direct Submission", Accession No. P54583, available online at <http://www.ncbi.nlm.nih.gov/protein/1708075/?report=genpept>, Aug. 1995, 6 pages.
Lindenmuth et al., "Production and Characterization of Acidothermus Cellulolyticus Endoglucanase in Pichia pastoris", Accession No. HQ541433, available online at <http://www.ncbi.nlm.nih.gov/nuccore/HQ541433>, 2011, 2 pages.
Nakamura et al., "Codon Usage Tabulated from International DNA Sequence Databases: Status for the year 2000", Nucleic Acids Research, vol. 28, No. 1, 2000, 1 page.
Nausch et al., "Expression and Subcellular Targeting of Human Complement Factor C5a in Nicotiana Species", Plos One, vol. 7, No. 12, Dec. 2012, pp. 1-13.
Paciorek et al., "Immunocytochemical Technique for Protein Localization in Sections of Plant Tissues", Nature Protocols, vol. 1, No. 1, 2006, pp. 104-107.
Rathmell et al., "Soluble Peroxidase in Fluid from the Intercellular Spaces of Tobacco Leaves", Plant Physiol., vol. 53, 1974, pp. 317-318.
Terry et al., "An Examination of Centrifugation as a Method of Extracting an Extracellular Solution from Peas, and Its Use for the Study of Indoleacetic Acid-induced Growth", Plant Physiol. vol. 66, 1980, pp. 321-325.

(Continued)

*Primary Examiner* — Cathy Kingdon Worley
(74) *Attorney, Agent, or Firm* — Morrison & Foerster LLP

(57) ABSTRACT

The present disclosure relates to methods of increasing the extraction of an apoplast-targeted recombinant protein in a plant tissue and to methods of increasing the purity of an apoplast-targeted recombinant protein recovered from a plant tissue. The methods involve contacting plant tissue with a rinse fluid on a plurality of occasions to release recombinant protein from the apoplast into the rinse fluid to create an apoplast wash fluid. The resulting content of the recombinant protein in the apoplast wash fluid is higher than the content of the recombinant protein in the apoplast wash fluid from comparable plant tissue contacted with rinse fluid on a single occasion.

11 Claims, 12 Drawing Sheets

(56) References Cited

OTHER PUBLICATIONS

Conrad et al., "Compartment-Specific Accumulation of Recombinant Immunoglobulins in Plant Cells: An Essential Tool for Antibody Production and Immunomodulation of Physiological Functions and Pathogen Activity", Plant Molecular Biology, vol. 38, 1998, pp. 101-109.
Delannoy et al., "Identification of Peptidases in Nicotiana Tabacum Leaf Intercellular Fluid", Proteomics, vol. 8, 2008, pp. 2285-2298.
Doran, Pauline M., "Foreign Protein Degradation and Instability in Plants and Plant Tissue Cultures", Trends in Biotechnology, vol. 24, No. 9, 2006, pp. 426-432.
Geldner, Niko, "The Plant Endosomal System-Its Structure and Role in Signal Transduction and Plant Development", Planta, vol. 219, 2004, pp. 547-560.
Hassan et al., "Considerations for Extraction of Monoclonal Antibodies Targeted to Different Subcellular Compartments in Transgenic Tobacco Plants", Plant Biotechnology Journal, vol. 6, 2008, pp. 733-748.
Hegde et al., "The Surprising Complexity of Signal Sequences", Trends in Biochemical Sciences, vol. 31, No. 10, 2006, pp. 563-571.
James et al., "Increased Production and Recovery of Secreted Foreign Proteins from Plant Cell Cultures using an Affinity Chromatography Bioreactor", Biochemical Engineering Journal, vol. 12, 2002, pp. 205-213.
Lombardi et al., "Optimisation of the Purification Process of a Tumour-Targeting Antibody Produced in N. Benthamiana using Vacuum-Agroinfiltration", Transgenic Res, vol. 19, 2010, pp. 1083-1097.
Menkhaus et al., "Considerations for the Recovery of Recombinant Proteins from Plants", Biotechnol. Prog., vol. 20, No. 4, 2004, pp. 1001-1014.
Sharp et al., "Strategies for Enhancing Monoclonal Antibody Accumulation in Plant Cell and Organ Cultures", Biotechnol. Prog., vol. 17, No. 6, 2001, pp. 979-992.
Surpin et al., "Traffic Jams Affect Plant Development and Signal Transduction", Nature Reviews Molecular Cell Biology, vol. 5, Feb. 2004, pp. 100-111.
Ting, Irwin P., "Matic Dehydrogenases in Corn Root Tips", Archives of Biochemistry and Biophysics, vol. 126, 2008, pp. 1-7.
Trudel et al., "Secreted Hen lysozyme in Transgenic Tobacco: Recovery of Bound Enzyme and in Vitro Growth Inhibition of Plant Pathogens", Plant Science, vol. 106, 1995, pp. 55-62.
Wilken et al., "Recovery and Purification of Plant-Made Recombinant Proteins", Biotechnology Advances, vol. 30, 2012, pp. 419-433.
Ziegelhoffer et al., "Dramatic Effects of Truncation and Sub-Cellular Targeting on the Accumulation of Recombinant Microbial Cellulase in Tobacco", Molecular Breeding, vol. 8, 2001, pp. 147-158.
Lindenmuth et al., "Production and Characterization of Acidothermus Cellulolyticus Endoglucanase in Pichia pastoris", Protein Expression and Purification vol. 77, 2011, pp. 153-158.

* cited by examiner

APOPLAST WASH FLUID RECOVERY FOR IMPROVED RECOMBINANT ENDOGLUCANASE EXTRACTION IN TABACCO LEAVES

CROSS-REFERENCE TO RELATED APPLICATION

This application claims the benefit of U.S. Provisional Application No. 61/712,774, filed Oct. 11, 2012, which is hereby incorporated by reference in its entirety.

STATEMENT REGARDING FEDERALLY-SPONSORED RESEARCH

This invention was made with government support under Grant No. 1067432 awarded by the National Science Foundation (NSF). The government has certain rights in the invention.

FIELD

The present disclosure relates to methods of increasing the production of an apoplast-targeted recombinant protein in a plant tissue and to methods of increasing the purity of an apoplast-targeted recombinant protein recovered from a plant tissue.

BACKGROUND

In planta production of apoplast-targeted cellulose degrading enzymes may be a valuable approach for efficient production of concentrated enzyme preparations that can be used for saccharification of cellulose in pretreated feedstocks. The use of agroinfiltration to produce heterologous proteins of interest (POI) in leaf tissue has been reviewed along with considerations affecting yield and downstream processing (Menkhaus T J et al., Biotechnology Progress, 20, 2004, 1001-1014). The benefits of obtaining a purified extract from plant tissue have been discussed previously (Hassan S et al., Plant Biotechnology Journal, 6, 2008, 733-748; Wilken L R et al., Biotechnology Advances, 30, 2012, 419-433), and a method for recovering apoplast wash fluid from leaf tissue has been described (Klement Z, Phytopathology, 55, 1965, 1033; Rathmell W G et al., Plant Physiology, 53, 1974, 317-318). However, traditional recovery methods, such as tissue homogenization, suffer from disadvantages including that high fiber content fouls chromatography columns, equipment is and operating costs are expensive, there is an increased likelihood of contaminant release, and air-liquid interfaces may damage protein (Hassan S et al., 2008, Plant Biotechnology Journal, 6, 733-748). Previous reports have used apoplast wash fluid (AWF) recovery to remove secreted recombinant POI from leaf tissue and quantified its recovery as a percent yield of the total protein expressed (Turpen T H et al., U.S.P. Office (Ed.), Large Scale Biology Corporation, USA, 2006, pp. 28; Lombardi R et al., Transgenic Research, 19, 2010, 1083-1097). However, protein degradation in leaf tissue, especially in the leaf apoplast, remains a major industrial impediment (Hehle V K et al., BMC Biotechnology, 2011; Doran P M, Trends in Biotechnology, 24, 2006, 426-432). Thus, there exists a need for improved methods of increasing the production and recovery of a protein of interest from the apoplast of plant tissues.

BRIEF SUMMARY

In one aspect, the present disclosure relates to a method of producing E1 endoglucanase in a leaf tissue, the method including: providing leaf tissue from *Nicotiana tabacum* transiently transformed to express E1 endoglucanase from *Acidothermus cellulolyticus* under the control of the CaMV 35S promoter, incubating the leaf tissue at 20° C. in a humid environment such that the E1 endoglucanase is expressed and located to an apoplast of a cell of the leaf tissue, contacting the leaf tissue with a rinse fluid using vacuum infiltration-centrifugation once every 24 hours over the course of 6 days to release the E1 endoglucanase from the apoplast into the rinse fluid to create an apoplast wash fluid, where content of the E1 endoglucanase in the apoplast wash fluid from leaf tissue contacted with rinse fluid once every 24 hours for 6 days is at least two-fold higher than the content of the E1 endoglucanase in the apoplast wash fluid from a comparable leaf tissue contacted with rinse fluid only at the end of the 6 days.

In another aspect, the present disclosure relates to a method of producing a recombinant protein in a plant tissue, the method including: providing a plant tissue transiently transformed with a nucleic acid encoding a recombinant protein in operable combination with a promoter, incubating the plant tissue under suitable conditions such that the recombinant protein is expressed and located to an apoplast of a plant cell of the plant tissue, contacting the plant tissue with a rinse fluid on a plurality of occasions over the course of a production interval to release the recombinant protein from the apoplast into the rinse fluid to create an apoplast wash fluid, where content of the recombinant protein in the apoplast wash fluid from plant tissue contacted with rinse fluid on a plurality of occasions is higher than the content of the recombinant protein in the apoplast wash fluid from comparable plant tissue contacted with rinse fluid only at the end of the production interval.

In some embodiments, the recombinant protein is a cellulase.

In some embodiments, the cellulase is E1 endoglucanase.

In some embodiments, the plant tissue is a leaf tissue.

In some embodiments, the leaf tissue is from *N. tabacum*.

In some embodiments, the plant tissue is transiently transformed using *Agrobacterium*.

In some embodiments, the promoter is a CaMV 35S promoter.

In some embodiments, the contacting step includes vacuum-infiltrating the plant tissue to produce a vacuum-infiltrated plant tissue submerged in the rinse fluid.

In some embodiments, the method further includes centrifuging the vacuum-infiltrated plant tissue to facilitate separation of the apoplast wash fluid from the plant tissue.

In some embodiments, force of the centrifuging step is not more than 30 kPa.

In some embodiments, centrifugation occurs for not more than 20 minutes.

In some embodiments, the rinse fluid includes a protein-stabilization agent.

In some embodiments, each occasion of the plurality of occasions occurs at a regular periodic interval over the course of the production interval.

In some embodiments, the regular periodic interval is about once every 24 hours over the course of the production interval.

In some embodiments, the production interval is about 6 days.

In some embodiments, at least a portion of the plant tissue remains viable after each occasion of the plurality of occasions.

In some embodiments, viable plant tissue remains capable of expressing the recombinant protein.

In some embodiments, content of the recombinant protein in the apoplast wash fluid from plant tissue contacted with rinse fluid on a plurality of occasions is at least two-fold higher than the content of the recombinant protein in the apoplast wash fluid from comparable plant tissue contacted with rinse fluid only at the end of the production interval.

In some embodiments, purity of the recombinant protein in the apoplast wash fluid from plant tissue contacted with rinse fluid on a plurality of occasions is at least 125-fold higher than the purity of the recombinant protein in the apoplast wash fluid from comparable plant tissue contacted with rinse fluid only at the end of the production interval.

In some embodiments, the method further includes recovering the recombinant protein from the apoplast wash fluid.

DESCRIPTION OF THE FIGURES

FIG. 3A illustrates vacuum infiltration of rinse fluid into the plant tissue and subsequent release of the vacuum. FIG. 3B illustrates the rinsing procedure as shown in FIG. 3A, with the addition of a centrifugation step following release of the vacuum to increase the release of protein from the apoplast.

FIG. 4A illustrates a 50 mL FALCON™ centrifuge tube (left) and collection caps (right) used to collect apoplast wash fluid (AWF). FIG. 4B illustrates the bottom view of the perforated bottom of the FALCON™ tube.

FIG. 6A illustrates yields of E1 endoglucanase catalytic domain (E1cd). FIG. 6B illustrates yields of total soluble protein (TSP). FIG. 6C illustrates yields of malate dehydrogenase (MDH). FIG. 6D illustrates yields of phenolics (presented in units of gallic acid equivalents, or GAE). The overall bar height represents the pooled yield of all extracts collected per leaf and the error bars represent the standard deviation of leaf-to-leaf variability of this value. The bar is further divided by shades of gray to show what portion of the overall yield was collected in which type of extract. The darkest shade is the fraction of the component that was collected daily between days 2 through 5 post-incubation by vacuum infiltration-centrifugation (VI-C), either in the apoplast wash fluid or rinse fluid; A+R (2 dpi-5 dpi). The lightest shade of gray represents the fraction of the components collected in apoplast wash fluid and rinse fluid during three rounds of VI-C all performed consecutively on the sixth and final day of incubation; A+R (1×-3×). The medium shade of gray depicts the fraction of the overall yield recovered by homogenate extraction on the final day of incubation after performing the three consecutive rounds of VI-C; this is the washed homogenate extract (WHE).

FIG. 7A illustrates E1 endoglucanase catalytic domain (E1cd) as a percent of the total soluble protein in apoplast wash fluid samples collected at the different days post-agroinfiltration (dpi), including three AWF samples produced upon consecutive washes on the sixth and final day (6 dpi-1× through 6 dpi-3×), for the leaf sets with and without multiple rounds of periodic rinsing. FIG. 7B illustrates that apoplast wash fluid (AWF) was collected daily on triplicate agroinfiltrated leaves with multiple rounds of periodic rinsing, starting from 2 days post-infiltration (dpi) and ending at 6 dpi. E1, TSP, MDH, and phenolics were assayed and the average for the three leaves for each component was calculated. This figure graphically depicts the changes in the yield per day, with the total amount collected in AWF during this period normalized to 100% for each component. For 6 dpi, only the AWF collected on the first round of VI-C was used for the calculations.

FIG. 8A illustrates percent (%) recovery of E1 or TSP over various days post inoculation (dpi). FIG. 8B illustrates the fold-improvement in purity of E1 recovered from apoplast wash fluid either with periodic rinsing or without periodic rinsing.

DETAILED DESCRIPTION

Figure 1:
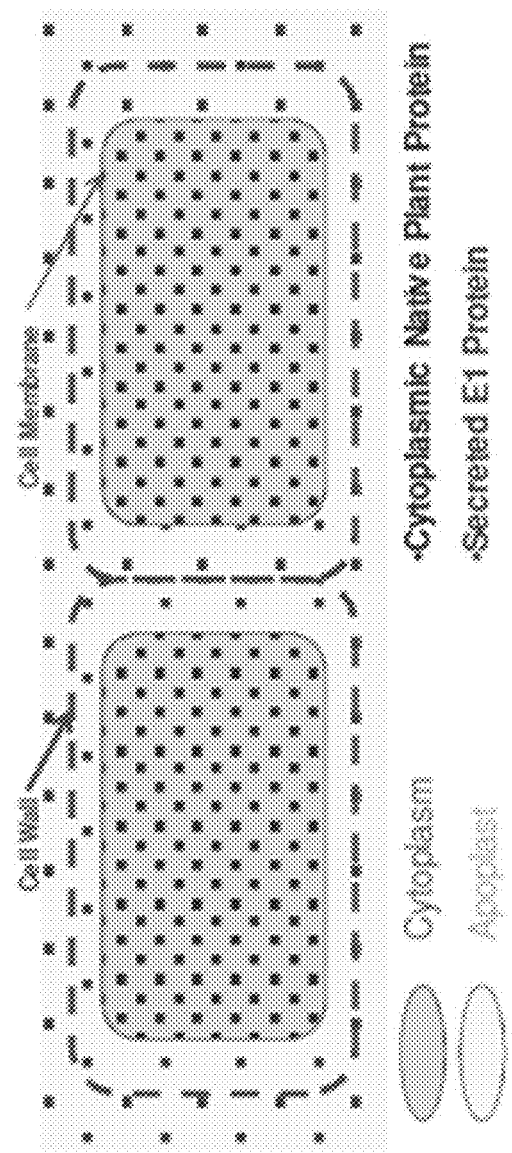
FIG. 1 illustrates that the location of secreted E1 protein is in the plant cell apoplast.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

The present disclosure relates to methods of increasing the production of an apoplast-targeted recombinant protein in a plant tissue and to methods of increasing the purity of an apoplast-targeted recombinant protein recovered from a plant tissue.

In particular, the present disclosure is based, at least in part, on Applicant's discovery that multiple rounds of periodic rinsing of plant tissues to release a protein from the apoplast, as opposed to non-periodic rinsing to release the protein, increases protein production and protein purity in the rinsed plant tissue, as well as results in increased protein recovery from the apoplast. The methods of the present disclosure employ non-destructive recovery methods to remove proteins of interest from leaf tissue while preserving the leaf tissue for its further production. These methods described herein may find use in improving protein yields, improving protein purity, and potentially improving leaf health.

The terms "decrease," "reduce" and "reduction" as used in reference to biological function (e.g., enzymatic activity, production of compound, expression of a protein, etc.) refer to a measurable lessening in the function by preferably at least 10%, more preferably at least 50%, still more preferably at least 75%, and most preferably at least 90%. Depending upon the function, the reduction may be from 10% to 100%. The term "substantial reduction" and the like refers to a reduction of at least 50%, 75%, 90%, 95% or 100%.

The terms "increase," "elevate" and "elevation" as used in reference to biological function (e.g., enzymatic activity, production of compound, expression of a protein, etc.) refer to a measurable augmentation in the function by preferably at least 10%, more preferably at least 50%, still more preferably at least 75%, and most preferably at least 90%. Depending upon the function, the elevation may be from 10% to 100%; or at least 10-fold, 100-fold, or 1000-fold up to 100-fold, 1000-fold or 10.000-fold or more. The term "substantial elevation" and the like refers to an elevation of at least 50%, 75%, 90%, 95% or 100%.

The terms "isolated" and "purified" as used herein refers to a material that is removed from at least one component with which it is naturally associated (e.g., removed from its original environment). The term "isolated," when used in reference to a recombinant protein, refers to a protein that has been removed from the culture medium of the host cell that expressed the protein. As such an isolated protein is free of extraneous or unwanted compounds (e.g., nucleic acids, native bacterial proteins, etc.).

As used herein, the singular form "a", "an", and "the" includes plural references unless indicated otherwise. For example, "a rinse" includes one or more rinses.

The phrase "comprising" as used herein is open-ended, indicating that such embodiments may include additional elements. In contrast, the phrase "consisting of" is closed, indicating that such embodiments do not include additional elements (except for trace impurities). The phrase "consisting essentially of" is partially closed, indicating that such embodiments may further comprise elements that do not materially change the basic characteristics of such embodiments. It is understood that aspects and embodiments described herein as "comprising" include "consisting" and/or "consisting essentially of" aspects and embodiments.

Transformation and Recombinant Proteins

The methods of the present disclosure involve transient transformation of a plant tissue to express a recombinant protein. Methods of transient transformation are well-known in the art and are described herein. Exemplary methods include the *Agrobacterium tumefaciens* transformation system. Suitable vectors for use in the transformation system are also well-known in the art. Transient transformation systems with plant tissues typically involve transforming a plant cell or tissue to express a recombinant nucleic acid operably linked to a promoter to drive expression of the nucleic acid. Methods of constructing recombinant nucleic acids and promoters are well-known in the art and are described herein. In some embodiments, plant tissues are transiently transformed to express a recombinant nucleic acid encoding an E1 endoglucanase operably linked to the CaMV 35S promoter. In some embodiments, the plant tissue to be transiently transformed in leaf tissue. Suitable conditions to facilitate transient transformation of the plant tissue are well-known in the art such as, for example, incubating the agroinfiltrated plant tissue at 20° C. in a humid environment.

Various recombinant proteins may be used in the methods of the present disclosure. Suitable recombinant proteins include those that are secreted to, targeted to, expressed in, or otherwise present in the apoplast of a plant cell. In some embodiments, the recombinant protein is E1 endoglucanase. Other exemplary proteins include, for example, those proteins that are useful in saccharification processes, such as cellulases, hemicellulases, pectinases, endoglucanases, exoglucanses, and other cell-wall degrading or cell-wall modifying proteins.

Rinsing Procedures

The methods of the present disclosure involve periodic rinsing of a transiently transformed plant tissue to release proteins from the apoplast so that the recombinant proteins can be recovered. Rinsing may refer to a process or series of processes that facilitate the release of a protein from the apoplast of a plant cell in a plant tissue. The methods of the present disclosure make use of periodic rinses to increase the total content of protein that can be recovered.

Following transformation of the plant tissue and once protein expression and secretion begins, the apoplast is rinsed to recover its components. In some preferred embodiments, rinsing is performed using vacuum infiltration-centrifugation (VI-C). By the VI-C method, the leaves are submerged in a rinse fluid that should be optimized for protein stabilization. To facilitate the infiltration, the rinse fluid typically would contain low levels of non-ionic surfactant, such as Silwet L-77. Leaves may be infiltrated individually or as a set within a large vacuum chamber in any orientation, although it is preferred that leaves be completely submerged with their abaxial (bottom) side facing up to facilitate the removal of air bubbles from their stomata. Various types of vacuum chamber or pump may be appropriate, but the vacuum pressure that is achieved should be able to go below 50 kPa, and an absolute pressure of at most 30 kPa at most is preferred. Vacuum pressure may be applied and released several times with the leaf or leaves still submerged, or the duration of the vacuum pressure application can be optimized, because it is preferable to achieve the greatest infiltrated volume per gram of leaf tissue. If vacuum pressure is applied multiple times per round of infiltration or if the leaves are submerged for a total duration longer than five minutes, it is recommended that the rinse fluid is collected as it will contain secreted recombinant protein with high purity. Furthermore, other methods of rinse fluid infiltration, such as pressure infiltration with a syringe, would be sufficient to produce the desired result while preventing leakage of the recombinant protein into the rinse fluid.

Figure 4:
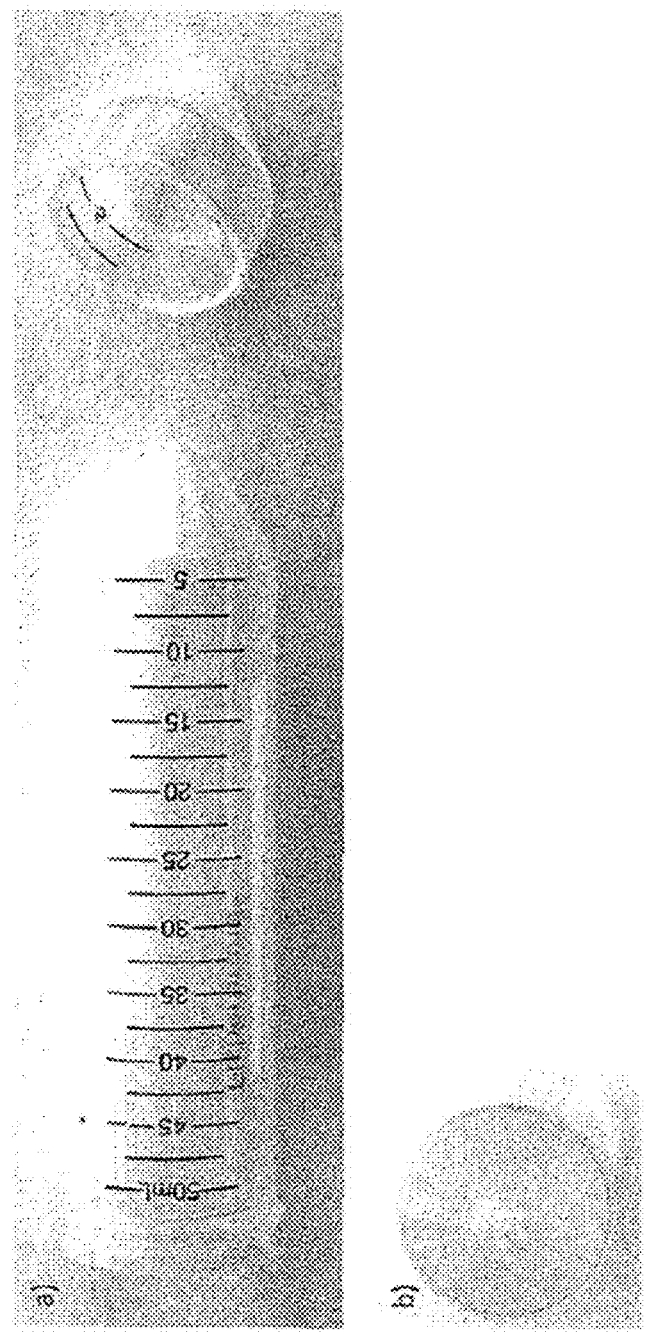
FIG. 4 illustrates an example of an apparatus used to collect apoplast wash fluid.

When using the vacuum infiltration-centrifugation method, the second step of the VI-C method is centrifugation of the whole leaves. A variety of centrifuges and apparatuses may be used for collection of the resulting fluid, called apoplast wash fluid (AWF), as described previously (Turpen T H et al., U.S.P. Office (Ed.), Large Scale Biology Corporation, USA, 2006, pp. 28), but they all should satisfy the general principle of allowing the centrifugal force to pull and separate the AWF from the leaves. The apparatus used may be a perforated 50 mL FALCON™ tube containing 7-12 pinholes approximately 3 mm in diameter at its conical bottom, as shown in FIG. 4. Pinhole size, orientation, and other parameters should not create pressure points on leaf and cause unnecessary damage to the tissue. Other designs may include hanging the leaf from the top of the tube using a hook or a clamp. The centrifugal force employed should be sufficient to recover apoplast wash fluid while not causing damage to the leaf, which can be in the form of crushing, tearing, or creasing. These damage marks, while largely acceptable when simply recovering AWF for a one-time extraction, can create necrotic regions in the tissue. To cause the least amount damage, leaves may be rolled into the form of a cylinder with its adaxial side face out. Then they may be folded lengthwise in half and loaded into the tube with the stem of the leaf resting on the tube's bottom. The stem itself may be cut as short as possible to the edge of the leafy tissue. The highest centrifugal force that could be employed in, for example, a BECKMAN™ GS-6KR centrifuge while consistently ensuring leaves were not damaged was 400*g for *Nicotiana tabacum* and 125*g for *Nicotiana benthamiana*. The duration of centrifugation may be as long as 20 minutes, after which it is unlikely that further AWF could be collected from the leaves at that force.

Figure 5:
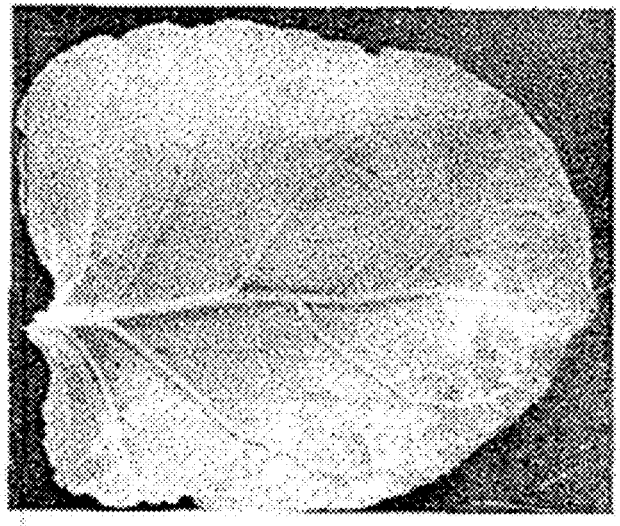
FIG. 5 illustrates a *Nicotiana benthamiana* leaf with an approximate fresh weight of 2 grams that had been centrifuged at 125*g in a perforated centrifuge tube, as seen in FIG. 4. The leaf was oriented in the tube by rolling into a cylinder, bending lengthwise halfway, and inserting with the truncated stem downwards. The leaf is mostly dry (light regions), but infiltrated fluid remains (dark regions). There is minimal damage to the leaf, as no creasing or tears are readily discernible.

After the centrifugation, the leaf may look dry (containing light regions), but often infiltrated fluid remains in the leaf (dark regions) (See FIG. 5). It is preferred in such instances to perform another round of VI-C to recover more AWF rather than increase the centrifugal force or risk damaging the leaf tissue. Indeed, as many rounds of VI-C per day as practical, such as 5 rounds of periodic rinsing on a single day, may be performed since the time required for each cycle is relatively short. Plant tissue that is periodically rinsed may remain viable and capable of continuing to produce recombinant protein. In some embodiments, the periodic rinsing occurs once every 24 hours. The frequency of periodic rinsing may be altered to be longer or shorter depending on the health of the sample leaves. When to perform the initial round of VI-C may also be optimized. For example, there may be improvements in the purity of the initial AWF and RF recovered if there was a round of VI-C prior to the agroinfiltration. In between intervals of periodic rinsing, and generally, leaves should remain incubated at 20° C. in a humid environment to prevent wilting and transpiration, which can negatively affect yield of AWF volume. The VI-C method may allow for 400 mL of rinse fluid per kg of fresh weight (but more typically, 300 mL/kg FW) to be moved into and out of, for example, a *Nicotiana tabacum* leaf tissue.

Periodic rinsing procedures using the methods of the present disclosure are performed over the course of a production interval. A production interval may refer to the period of time during which a transiently transformed plant tissue expresses a recombinant protein. In some embodiments, the production interval is 6 days and plant tissue is periodically rinsed every 24 hours (i.e. the plant tissue is rinsed a total of 6 times, once every 24 hours, over the course of 6 days). After each occasion of contacting the plant tissue with a rinse fluid using the rinsing procedures described herein, the apoplast wash fluid containing the recombinant protein isolated from the apoplast of a plant cell in the plant tissue may be recovered and various aspects of the recovered recombinant protein may be analyzed.

The periodic rinsing procedures of the present disclosure result in greater recombinant protein content in the apoplast wash fluid from plant tissue contacted with rinse fluid using periodic rinsing as compared to the content of the recombinant protein in the apoplast wash fluid from comparable plant tissue contacted with rinse fluid only at the end of the production interval. For example, when the plant tissue is rinsed a total of 6 times, once every 24 hours, over the course of 6 days (a 6 day production interval), the total recovered protein from the combination of all 6 recovered apoplast wash fluids is greater than the total recovered protein from plant tissue that was rinsed only on day six (the last day of the production interval). Periodic rinsing may also result in a higher protein content in the apoplast wash fluids from plant tissue subjected to periodic rinsing as compared to a comparable plant tissue where apoplast wash fluid was never recovered.

EXAMPLES

To better facilitate an understanding of the embodiments of the disclosure, the following examples are presented. The following examples are merely illustrative and are not meant to limit any embodiments of the present disclosure in any way.

Example 1

Periodic Method for Recovering Recombinant Proteins from the Interstitial Fluid of Agroinfiltrated *Nicotiana tabacum* Leaves The following Example describes a vacuum infiltration-centrifugation method developed for the recovery of transiently-produced cellulase enzymes in the apoplast wash fluid (AWF) of tobacco leaves. A single AWF recovery at the time of peak production following transient agroinfiltration of harvested tobacco leaves removes up to 67% of the *Acidothermus cellulolyticus* thermostable endo-1,4-β-glucanase catalytic domain (E1cd) activity. However, recovering AWF daily from agroinfiltrated leaves more than tripled the amount of the enzyme activity recovered in the AWF and doubled the amount of active E1cd produced overall. Rinsing the apoplast of agroinfiltrated leaves during the production/incubation period has potential advantages of improved protein stability, secretion kinetics, and leaf health. The AWF collected also had higher purity and enzyme concentration, up to 124- and 19-fold improvements respectively compared to recovery from homogenate extracts, facilitating its use in the saccharification process.

Materials and Methods

Transient Transformation of Plant Tissue

In the present Example, the *Agrobacterium* T-DNA expression system was used to house a constructed expression cassette employing the CaMV 35S promoter to drive the expression of the E1 endoglucanase from *Acidothermus cellulolyticus* fused to a rice amylase signal peptide, which is responsible for secreting E1 to the apoplast of a plant cell. E1 has an optimum temperature for activity of 81° C. The expression cassette was transformed into *Agrobacterium tumefaciens* using standard molecular biology protocols. The *Agrobacterium* housing the expression cassette was transformed into *N. tabacum* using vacuum infiltration at 30 kPa absolute pressure. After the agroinfiltration, leaves are incubated in a humid environment with the infiltrated *Agrobacterium* to allow gene transfer to occur, allowing for constitutive expression of the recombinant E1 protein and secretion into the apoplast of plant cells in the plant tissue (see FIG. 1).

Vacuum Infiltration-Centrifugation

Figure 2:
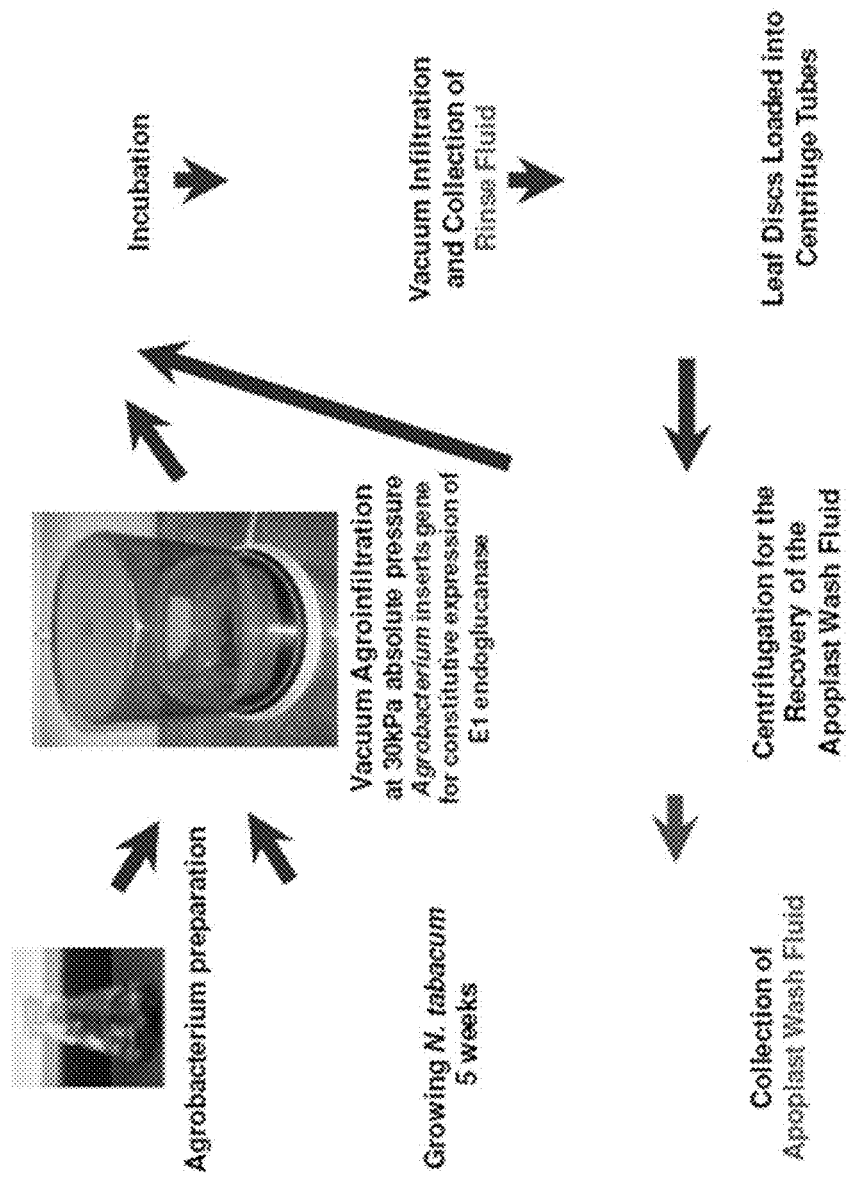
FIG. 2 illustrates an exemplary embodiment of transformation and rinsing steps used in the methods described herein to increase E1 endoglucanase protein production in *N. tabacum*.
Figure 3:
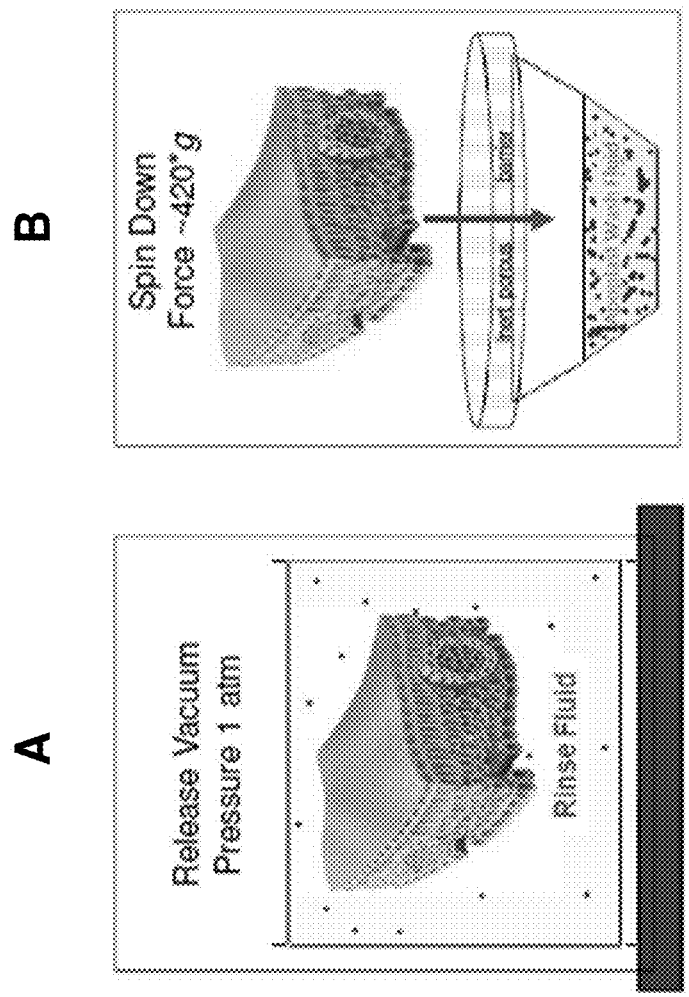
FIG. 3 illustrates exemplary embodiments of different rinsing procedures to release proteins from the apoplast of plant cells.

After the incubation period, (one set, n=2) of transiently transformed leaves were transferred to a 50 mL FALCON™ tube (FIG. 4) and rinse fluid was added to the tube, submerging the leaf in rinse fluid. Rinse fluid was vacuum infiltrated into the leaf tissue under a pressure of 1 atm, followed by a release of the vacuum. This results in some protein product leaching into the rinse fluid. After the vacuum was released, the leaf tissue in the rinse fluid was centrifuged at a force of ~420*g for 20 minutes, which presses the tissue flat against a biologically inert porous barrier, squeezing the apoplast wash fluid out of the leaf while preserving the leaf as a whole (See FIG. 2, FIG. 3, FIG. 4). After centrifugation, the infiltrated leaf appeared dry, but some infiltrated rinse fluid remained in the intact leaf.

For the leaf tissues subjected to multiple rounds of rinsing and collection of apoplast wash fluid, the first rinse (vacuum infiltration-centrifugation) occurred two days post inoculation with *Agrobacterium*. The rinsing procedure was then performed on the same plant leaf every 24 hours until the sixth day post inoculation. For the leaf tissue not subjected to periodic daily rinsing and collection of apoplast was fluid (one set, n=3), the leaf tissue was incubated with *Agrobacterium* for six days, and then subjected to rinsing (vacuum infiltration-centrifugation) on the sixth day post inoculation. The rinse fluid and/or apoplast wash fluid from all samples was collected and analyzed.

Biochemical Assays

E1 degrades 4-methylumbelliferyl-β-D-cellobioside (MUC) into cellobiose and the fluorescent marker 4-methylumbelliferose (MU) with a reported specific activity of 40 $\mu mol\ MU*min^{-1}*mg^{-1}$ enzyme (Ziegelhoffer et al., Molecular Breeding, 8, 2001, 147-158). Total soluble protein (TSP) was measured using Bradford reagent.

Results

Figure 6:
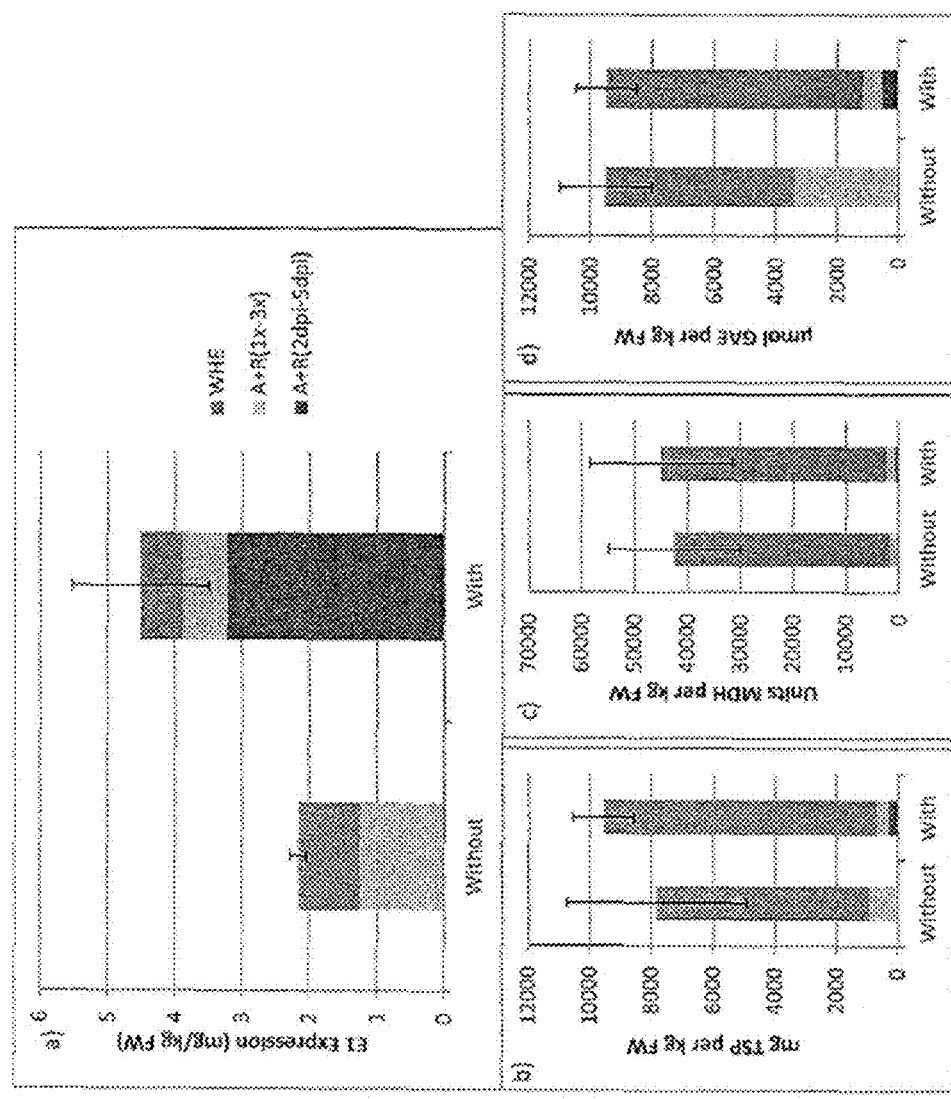
FIG. 6 illustrates the yields of various compounds in agroinfiltrated leaves measured following either multiple rounds of periodic rinses using vacuum infiltration-centrifugation (VI-C), or a single rinse of vacuum infiltration-centrifugation.

For E1 expressing agroinfiltrated leaves processed with the periodic rinsing and recovery method, rinse fluid (RF) and apoplast wash fluid (AWF) were recovered daily from 2 days post infiltration (dpi) to 5 dpi. At 6 dpi, alongside leaves processed without daily recovery (i.e. E1 was left to accumulate in the leaf during the entire incubation period), three rounds (1x-3x) of AWF recovery were performed prior to obtaining homogenate extract (HE). As can be seen in FIG. 6A, E1 yields more than doubled in leaves with daily recovery, 90% of which was collected in clarified AWF or RF. Overall, leaves subjected to the periodic rinsing and recovery method expressed significantly greater quantities of E1cd (mass quantification of E1cd is based on measuring the endoglucanase activity and converting to mass using the specific activity) as compared to leaves not subject to daily periodic rinsing.

Meanwhile, the yields of TSP or other assayed components not shown were not significantly affected by the periodic rinsing process and primarily stayed with the intact leaf tissue. Also, intracellular marker malate dehydrogenase (MDH) and phenolics did not have their yields significantly affected by periodic rinsing (FIG. 6B-FIG. 6D).

Figure 7:
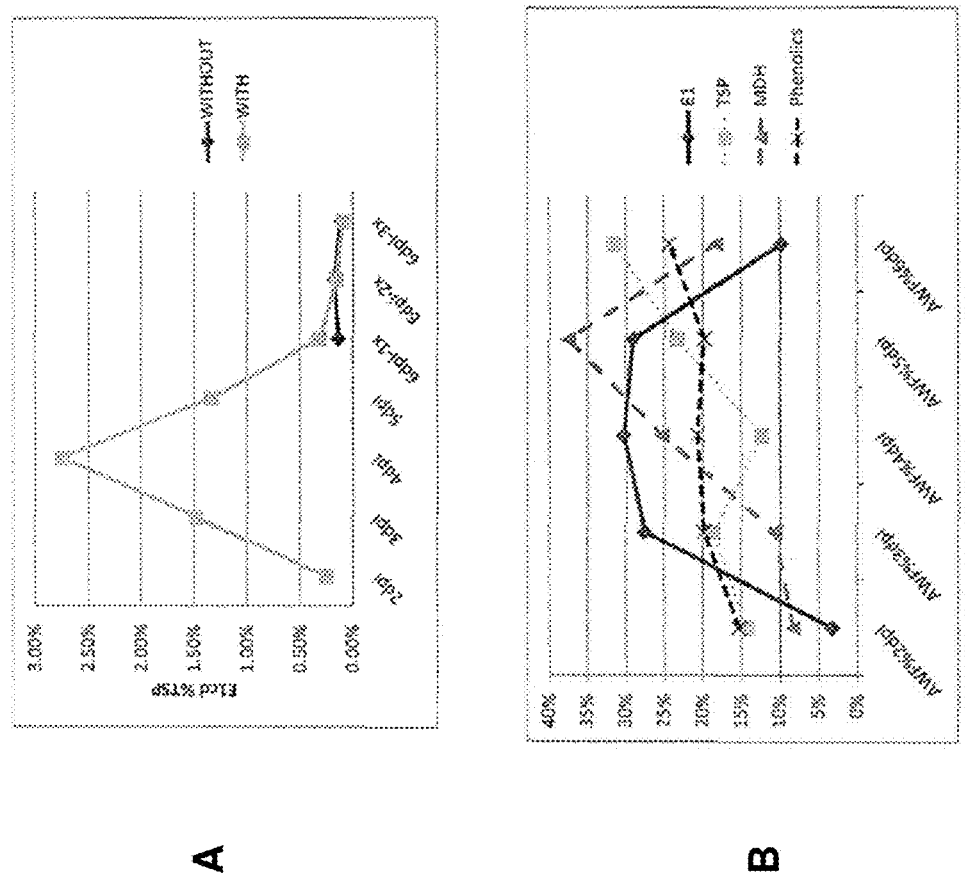
FIG. 7 illustrates comparisons of yields.

Furthermore, because E1cd is primarily secreted and the other assayed components are primarily retained by the plant cells, E1cd was selectively recovered in AWF during all rounds of VI-C. In leaves agroinfiltrated without applying the periodic rinsing (using VI-C as the rinsing procedure) and homogenized without applying any rounds of VI-C at any point, E1cd as a percent of total soluble protein was on average 0.022%, whereas the purity of the E1cd in AWF was as high as 2.751% on the 4th day post-infiltration, an improvement of 125-fold (FIG. 7A). Meanwhile, the highest purity of AWF from agroinfiltrated leaves without the periodic rinsing was 0.175%, which was only an 8-fold improvement on the homogenate extract and a 16-fold drop from 4 dpi AWF that applied the periodic rinsing.

The peak purity being achieved in the AWF at 4 dpi corresponds with peak secretion of E1cd at that day, observed by comparing the yields at the different dpi (FIG. 7B). Of all the components tested, only the heterologous secreted protein E1cd had a pattern that showed peak recovery by AWF between 3 dpi and 5 dpi, suggesting that this was when its expression was highest as well. The other components either remained steady (phenolics) or showed slight increases of intracellular contamination over time (MDH and TSP).

Figure 8:
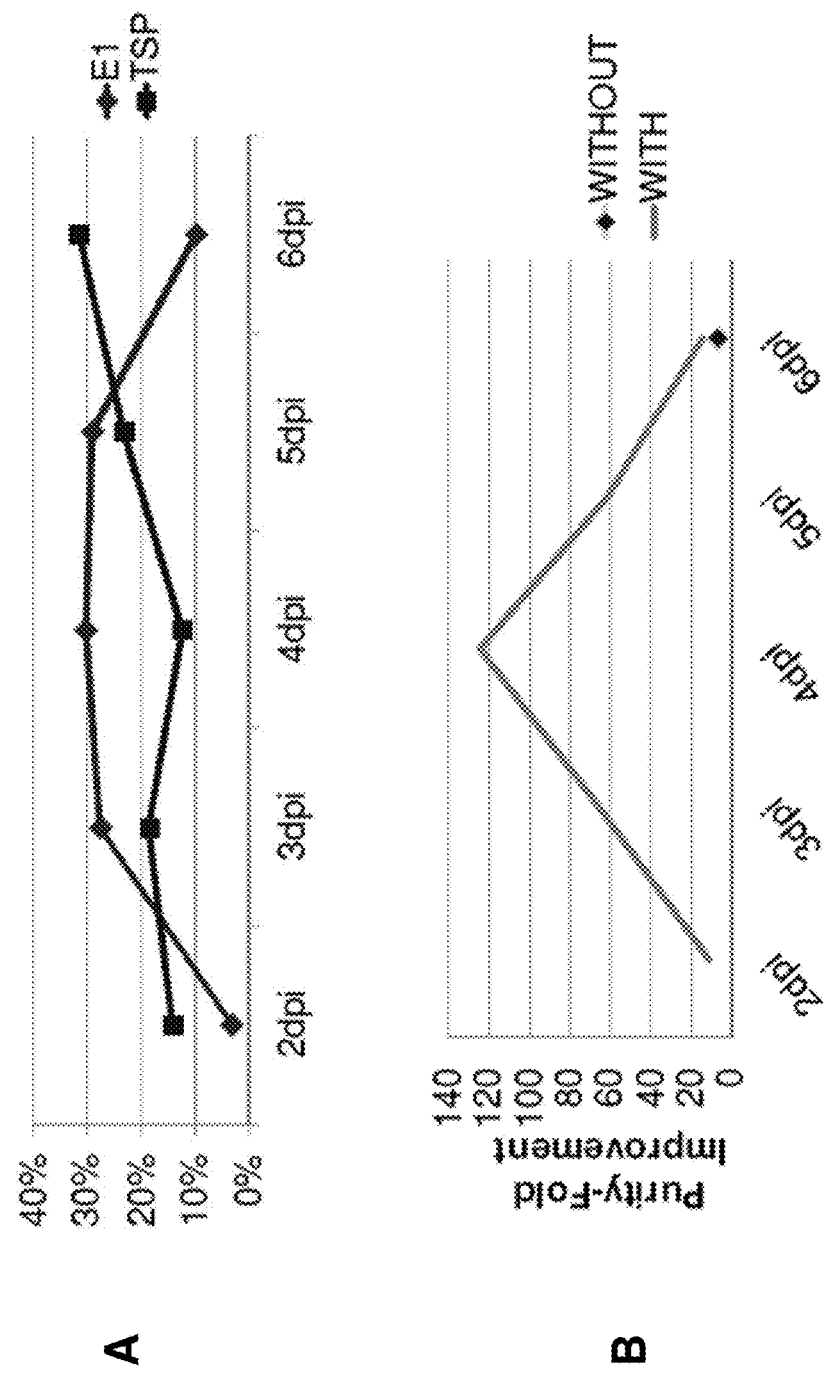
FIG. 8 illustrates that E1 endoglucanase purity was amplified by periodic AWF recovery.

The periodic daily rinsing method also increased the purity of recovered E1 protein. In leaves with daily rinsing and recovery, out of all of the E1 recovered in AWF (not including AWF from rounds two and three at 6 dpi), 87% was recovered between three and five dpi, peaking at 4 dpi, whereas for TSP this was only 54%, peaking at 6 dpi as leaves began to deteriorate (FIG. 8A). Purity of the AWF was highest at 4 dpi in this experiment, 124 times more pure than HE from leaves without the periodic rinsing method at 6 dpi and 19 times more pure than their AWF (FIG. 8B).

Table 1 and Table 2 contain a detailed summary of the data from this experiment. The tables show average yields of the various components tested expressed in their respective units in the extracts collected from whole leaf sets of five-week-old *Nicotiana tabacum* leaves agroinfiltrated to express endoglucanase catalytic domain (E1) without (Table 1; n=2) and with (Table 2; n=3) the periodic daily rinsing method. AWF (1-3): Apoplast wash fluid collected after rounds one through three of centrifugation. RF (1-3): Rinse fluid collected after rounds one through three of infiltration. WHE: Washed homogenate extract, derived from the processed (washed) leaf strips. UHE: Unwashed homogenate extract, derived from unprocessed leaf strips. Dpi: days post-infiltration on which the AWF or RF was collected for the leaves subjected to periodic daily rinsing.

TABLE 1

Data from leaves without periodic daily rinsing

| Component Units | E1 cd Activity milligrams per kg FW | Total Soluble Protein milligrams per kg FW | Malate Dehydrogenase Enz. Units par kg FW | Phenolics Content μmol Gallic Acid Eq. per kg FW |
|---|---|---|---|---|
| AWF1 | 0.56 ± 0.04 | 394 ± 161 | 50 ± 60 | 321 ± 249 |
| AWF2 | 0.25 ± 0.01 | 140 ± 60 | 51 ± 18 | 281 ± 269 |
| AWF3 | 0.16 ± 0.13 | 141 ± 10 | 60 ± 36 | 287 ± 20 |
| RF1 | 0.13 ± 0.01 | 146 ± 6 | 620 ± 98 | 688 ± 374 |
| RF2 | 0.10 ± 0.05 | 43 ± 11 | 442 ± 101 | 856 ± 318 |
| RF3 | 0.06 ± 0.04 | 61 ± 15 | 408 ± 125 | 988 ± 237 |
| WHE | 0.91 ± 0.30 | 6933 ± 3120 | 40768 ± 12142 | 6094 ± 2447 |
| UHE | 2.26 ± 0.96 | 10222 ± 343 | 34731 ± 10358 | 8864 ± 506 |
| % yield = (ΣAWF + ΣRF)ΣRHS | 58% ± 11% | 13% ± 8% | 4% ± 1% | 37% ± 16% |
| % Error in MB | 0% ± 38% | 29% ± 40% | −20% ± 1% | −7% ± 21% |

TABLE 2

Data from leaves with periodic daily rinsing

| Component Units | E1 cd Activity milligrams per kg FW | | Total Soluble Protein milligrams per kg FW | | Malate Dehydrogenase Enz. Units par kg FW | | Phenolics Content μmol Gallic Acid Eq. per kg FW | |
|---|---|---|---|---|---|---|---|---|
| AWF1 | 0.31 ± 0.07 | | 97 ± 9 | | 75 ± 12 | | 67 ± 15 | |
| AWF2 | 0.11 ± 0.04 | | 73 ± 13 | | 52 ± 32 | | 66 ± 25 | |
| AWF3 | 0.09 ± 0.06 | | 96 ± 6 | | 76 ± 13 | | 111 ± 4 | |
| RF1 | 0.07 ± 0.02 | | 40 ± 13 | | 631 ± 107 | | 145 ± 46 | |
| RF2 | 0.05 ± 0.02 | | 24 ± 0 | | 426 ± 17 | | 158 ± 125 | |
| RF3 | 0.03 ± 0.01 | | 32 ± 14 | | 445 ± 56 | | 139 ± 48 | |
| WHE | 0.63 ± 0.15 | | 8875 ± 971 | | 42664 ± 13327 | | 8290 ± 1001 | |
| UHE | 1.53 ± 0.65 | | 10657 ± 980 | | 46834 ± 8292 | | 9826 ± 1898 | |
| % yield = (ΣAWF + ΣRF)ΣRHS | 51% ± 2% | | 4% ± 0% | | 4% ± 1% | | 8% ± 2% | |
| % Error in MB | 13% ± 54% | | 14% ± 19% | | 8% ± 14% | | 8% ± 30% | |
| AWF 2 dpi | 0.11 | 0.05 | 44 | 1 | 34 | 13 | 41 | 1 |
| AWF 3 dpi | 0.84 | 0.13 | 57 | 2 | 43 | 14 | 54 | 6 |
| AWF 4 dpi | 1.04 | 0.68 | 38 | 5 | 104 | 28 | 57 | 14 |
| AWF 5 dpi | 0.96 | 0.46 | 72 | 11 | 158 | 65 | 55 | 15 |
| RF 2 dpi | 0.01 | 0.00 | 19 | 0 | 11 | 13 | 107 | 14 |
| RF 3 dpi | 0.07 | 0.00 | 37 | 1 | 25 | 12 | 66 | 17 |
| RF 4 dpi | 0.09 | 0.02 | 25 | 11 | 19 | 8 | 31 | 16 |
| RF 5 dpi | 0.11 | 0.04 | 50 | 12 | 207 | 34 | 88 | 28 |
| LEAF TOTAL | 4.51 | 1.02 | 9576 | 980 | 44970 | 13434 | 9475 | 973 |

Conclusion

Periodic daily rinsing and apoplast fluid wash recovery, when performed daily by a vacuum infiltration-centrifugation technique, more than doubled the yields of endoglucanase in agroinfiltrated *N. tabacum* leaves. This method more than tripled the amount of endoglucanase recovered in apoplast wash fluid and rinse fluid without increasing the recovery of contaminating proteins. The peak range of production and apoplast wash fluid recovery for endoglucanase in these leaves was observed at the fourth day postinfiltration, at which day purity was improved by two orders of magnitude over conventional methods. Without wishing to be bound by theory, recovery of endoglucanase from the leaves prior to its degradation in the apoplast was the most likely mechanism for these improved results.

Advantages of the periodic rinsing method include separation of the protein-rich cell interior (the symplast) from the relatively protein-poor cell exterior (the apoplast), that recovering just apoplast fluid will yield a sample enriched with highly purified and highly concentrated E1, that recovery while keeping the leaf intact allows further production, and that recovery of recombinant protein sooner after its production protects it from degradation, resulting in superior overall yields.

Performing the vacuum infiltration centrifugation method prior to the stage of incubation where expression is highest also cleared out the apoplast so that subsequent AWF recovered at later days post incubation had fewer contaminating proteins, which resulted in a more purified product than what otherwise could be achieved. As protein degradation in leaf tissue, especially in the leaf apoplast, is a major industrial impediment, this method may also offer the advantage of earlier recovery and storage of unstable proteins of interest into buffers optimized for preservation. The method may also clean the leaf from toxic components that plant cells secrete as part of the hypersensitive response, which results in regional necrosis (Kuta D D et al., African Journal of Biotechnology, 4, 2005, 752-757).

Similar protein yield improvements have been observed for a shake flask growing *Nicotiana tabacum* cells in an affinity column bioreactor (ACBR) (James E et al., Biochemical Engineering Journal, 12, 2002. 205-213. In that study, the installation and the daily cycling of culture media through an affinity chromatography column to recover secreted product (either heavy chain mouse monoclonal antibody and expressing granulocyte macrophage colony-stimulating factor; GM-CSF) increased yields up to eight-fold. It was shown that the concentration of GM-CSF in the culture media in an ACBR was able to rebound after recovery everyday back to the levels observed in a control shake flask that did not employ periodic recovery methods. This study credited the success in improving yields to removing the protein from a degradative environment, citing the correlation between observed yield improvement-fold and protein instability in culture media. However, in contrast to the design and results of James et al, the periodic daily rinsing method described herein utilizes intact leaf tissue grown in a greenhouse (it could also be grown in the field) and transient expression using vacuum agroinfiltration, rather than stable transgenic plant cells grown in suspension culture in a bioreactor.

The recombinant protein tested for this study was the catalytic domain of E1 endoglucanase (Ziegelhoffer T et al., Molecular Breeding, 8, 2001, 147-158), but the methods may also apply to any secreted recombinant protein that remains stable throughout an apoplast wash fluid (AWF) recovery. The host plant in this study was *Nicotiana tabacum*, but other plants are also imagined to be suitable plants for the methods described herein where agroinfiltration has shown to be effective, such as *Nicotiana benthamiana*, grape, and lettuce. AWF recovery was used for the removal of proteins as it was optimal for preserving leaf health while efficiently achieving high yield, but periodic recovery by other processes may also be possible, such as passive diffusion or repeated vacuum infiltrations, would also be effective in increasing expression. The period tested in this experiment was 24 hours, but a wide range of intervals between recoveries could also be effective.

The data presented suggests that periodic daily rinsing improves the expression and recovery of secreted heterologous proteins from agroinfiltrated leaves. Periodic daily rinsing employs non-destructive recovery methods to remove protein of interest from leaf tissue while preserving the leaf tissue for its further production. The method has advantages in improving yields, improving purity, and potentially improving leaf health.

Example 2

Increased Expression from *Nicotiana benthamiana* Leaves by Implementing Daily Cycles of Vacuum Infiltration and Centrifugation to Recover Apoplast Wash Fluid This Example illustrates that by the daily application of a vacuum infiltration-centrifugation method on agroinfiltrated *Nicotiana benthamiana* leaves, yields of transiently expressing E1 endoglucanase catalytic domain (E1cd) from *Acidothermus cellulolyticus* improved 2.2-fold. The resulting apoplast wash fluid (AWF) was enriched with purified recombinant protein while leaving the leaf intact and as phenotypically healthy as unperturbed control leaves. AWF was up to 17-fold more pure than homogenate extracts and removed on average 84% of the expressed E1cd. While AWF recovery is highly efficient for recovering secreted proteins from the interstitial spaces of leaf tissue, apoplast localization has been associated with proteolytic degradation which lowers overall yields. By recovering recombinant protein as it is being produced by the leaf instead of allowing it to incubate in the apoplast, daily apoplast wash fluid recovery represents a mechanism for improving overall yields from transiently expressing leaf tissue.

Introduction

The method of apoplast wash fluid (AWF) recovery has been used to recover the interstitial fluid of leaf tissue for decades (Klement 1965; Lohaus et al. 2001; Rathmell and Sequeira 1974; Terry and Bonner 1980). In more recent times, this has been useful for the recovery of secreted recombinant proteins from transiently expressing or transgenic tobacco (Lombardi et al. 2010; Trudel et al. 1995; Turpen et al. 2006; Ziegelhoffer et al. 2001). There are advantages of recovering recombinant protein with AWF as the primary extraction method rather than homogenization (wet grinding, extraction with liquid nitrogen, etc.) that may permit direct utilization of the fluid or at least improve performance of downstream chromatography columns, depending on the application. These include: far fewer contaminating intracellular proteins, lower sample volumes, less fiber, less phenolics, and less damage to the recombinant proteins (Hassan et al. 2008; Wilken and Nikolov 2012).

In principle, the AWF method recovers just the extracellular fluid while the rest of the tissue, including the extracellular matrix, the cells, and everything within the cells remain intact. This is what makes the method so powerful, but it also requires that the recombinant proteins of interest must be secreted into the apoplast. This is solved from a technical standpoint by including within the gene construct signal peptides which direct the endomembrane system to shuttle the proteins out of the cell by exocytosis (Geldner 2004; Hegde and Bernstein 2006).

However, some studies have demonstrated that overall yields of recombinant proteins are less if the protein is targeted to the apoplast than if they are targeted to other organelles (Conrad and Fiedler 1998; Hellwig et al. 2004; Nausch et al. 2012). Indeed, the apoplast is an environment rich in proteases, which may lead to the relative instability of recombinant proteins that are targeted there (Delannoy et al. 2008; Doran 2006). Additionally, the endomembrane system may experience traffic jams, bottlenecking the secretion pathway and perhaps reducing yields that way (Surpin and Raikhel 2004).

In plant cell cultures, yields of secreted recombinant proteins may be enhanced as much as 8-fold by their continuous harvest from the cell media (Sharp and Doran 2001; Smith et al. 2005). It was desired to bring about a similar result but for leaf tissue since the cost of growing plants is substantially less than that for purchasing, maintaining, operating, and cleaning bioreactors.

Materials and Methods

Plant Material

*Nicotiana benthamiana* (GRIN Accession #: TW16) (USDA 2012) and *Nicotiana tabacum* var. *Xanthii* (from Bryce Falk Lab, UC Davis Plant pathology) were grown from seed in a greenhouse with a temperature range of 25° C.-42° C. and observed averages of 31° C.±5° C. and an observed average absolute humidity of 12±2 g/m$^3$. Two weeks after seeding, seedlings were transplanted three in a 6" pot with Sunshine Mix #1 soil (SUN GRO™ Horticulture, Vancouver, BC). Pots were watered twice a day by an automated irrigation system and a custom fertilizer injection system comprising twelve essential plant nutrients. Five-week-old *N. benthamiana* plants were brought to the lab whole, and prior to the incubation or agroinfiltration the most recent mature leaves (between the third to the fifth leaf from the meristem) were excised.

E1 Constructs

The gene for full-length E1 endoglucanase from *Acidothermus cellulolyticus* (NCBI Accession #: P54583) was truncated by removing the sequences for the cellulose binding domain and the linker region. The 41 amino acid native signal peptide was removed from the N-terminus and replaced with the RAmy3D signal peptide from the α-amylase gene from *Oryza sativa* (NCBI Accession #: M59351.1). To the C-terminus, a 6-His tag was added. The construct was placed under the control of the CaMV 35S promoter. The resulting sequence was then codon-optimized using GeneDesigner software (version 1.1.4.1, DNA 2.0, Burlingame, Calif.) and the codon usage table for *N. benthamiana* (Nakamura et al. 2000). The sequence and the gene in entirety were submitted to GenBank (Accession #: HQ541433). The constructs for the truncated protein were synthesized and then propagated in *E. coli* before transformation into *Agrobacterium tumefaciens* EHA105 pCH32.

Agroinfiltration

Transformed *A. tumefaciens* were thawed from glycerol stocks and grown in small volumes of Luria-Bertani (LB) medium in round-bottom 10 mL tubes at 28° C. in an incubator shaking at 250 rpm. Once turbid, cultures were then inoculated 1% v/v into 200 mL LB medium and incubated again for 30 h at 28° C. and 250 rpm. After growth, the bacteria were centrifuged for 20 min at 3,200 g. The pellet was resuspended in activation solution consisting of 0.5M 2-(N-morpholino) ethanesulfonic acid (pH=5.6), 1.0M $MgCl_2$, 100 mM acetosyringone (3',5'-Dimethoxy-4'-hydroxyacetophenone) (Aldrich Chemicals, Milwaukee, Wis.) to an optical density at 600 nm of 0.5, as measured by a SPECTRAMAX™ M2 spectrophotometer (Molecular Devices, Sunnyvale, Calif.). In the activation solution, the bacteria cultures were incubated in the dark for two to five hours, and just prior to agroinfiltration 0.02% v/v SILWET L-77™ Seeds, Round Rock, Tex.) was added.

Detached plant leaves were held submerged into activated *Agrobacterium* solution in a plastic container by a plastic lined wire mesh. Three rounds of vacuum infiltration were applied in a 5-gal NALGENE™ vacuum chamber, where for each round the pressure was allowed to reach an absolute pressure of 30 kPa and held at that pressure for at least 30 s. Leaves were then patted dry with paper towels and allowed to dry on a rack for an hour prior to incubation.

Incubation

Incubation was performed in a 19"×14"×7" air-tight plastic storage box. Perlite soil additive (E.B. Stone Organics, Suisun City, Calif.) was submerged in DI water for at least three hours and poured into the box to create a layer about 4 cm thick to maintain humidity throughout the incubation. Plastic lined steel mesh was fit into the box to suspend the leaves about 4 cm above the Perlite layer. The box with detached leaves was incubated in the dark at 20° C., but the box was opened daily for examination of leaf weight and appearance and also so leaves from which AWF was recovered daily could be processed.

Daily Apoplast Wash Fluid Recovery

Leaves selected for daily recovery of AWF were processed every 24 h starting from two days after agroinfiltration. It was desired to only vacuum infiltrate with harvest buffer the right side of the leaf while leaving the left side dry. To do this, a plastic sheath was cut into which the left side of the leaf and midrib could loosely fit. The leaf was then affixed laterally to a side of a plastic container so that the right side and the edge of the sheath were submerged while the midrib and the left side of the leaf were suspended above the buffer surface. It was ensured that no regions on the left side were ever infiltrated, which would have resulted in contamination of right side AWF sample with left side yield upon centrifugation. The harvest buffer consisted of 50 mM sodium acetate (pH=5.5), 100 mM NaCl, and 0.02% SILWET L-77™ and was used for vacuum infiltration at 20° C.-25° C. The plastic container with buffer and leaf was placed in a NALGENE™ container for vacuum application.

Figure 9:
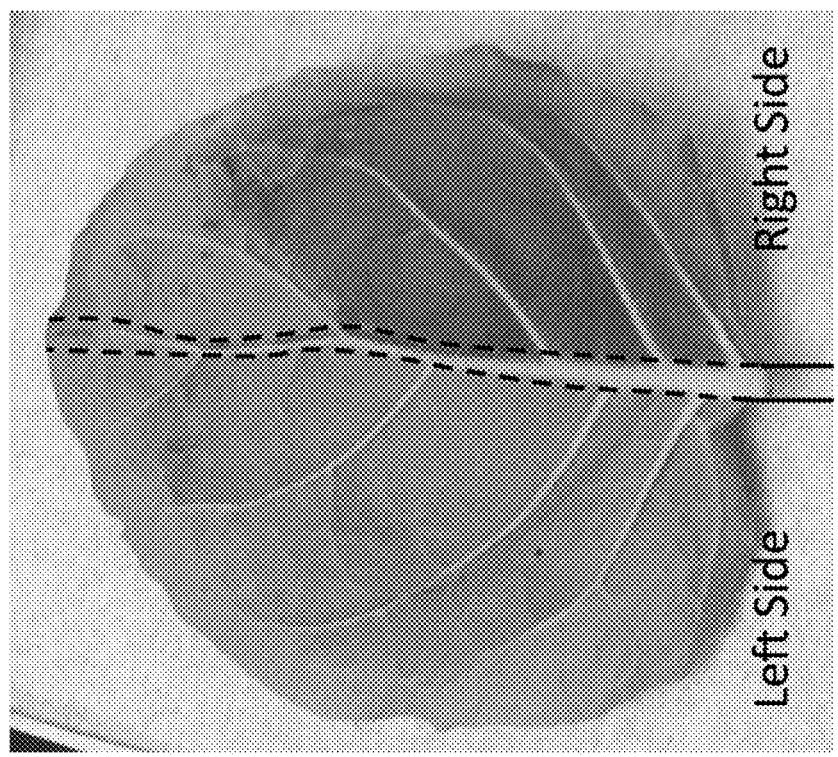
FIG. 9 illustrates a typical half-infiltrated leaf, prior to centrifugation, showing the dry regions (light) and the buffer infiltrated regions (dark) and defining the left and right sides of the leaf. Hashed lines depict the path of the razor excising of the tissue for homogenization.

Excessive vacuum application was correlated to premature leaf necrosis in preliminary experiments, a technical challenge since this method for infiltrated halves of whole leaves was less efficient consistently saturating leaf tissue. Vacuum in the chamber was never allowed to drop below 23 kPa absolute pressure, the number of applications was never allowed to exceed 5 cycles (each cycle included the time to increase vacuum pressure to the desired amount, holding that pressure for 30 s, and releasing vacuum for 30 s), and the total amount of time the tissue was submerged in buffer was never allowed to exceed 15 minutes at a time. For leaves at earlier dpi, this meant that some regions of the right side of the leaf might not have been completely saturated with buffer. For example, typically the top part of the right side of the leaf remained dry (FIG. 9). As the experiment progressed, vacuum pressure was only as strong and the number of applications only as many as needed to saturate the leaf tissue with buffer, amounts that varied leaf-to-leaf and day-to-day. By 7 dpi, the right side of most leaves required only about 50 kPa of absolute pressure to fully infiltrate the tissue with one vacuum application.

Centrifugation was performed to minimize damage to leaf tissue, which in turn would promote continued leaf health and yields of recombinant protein. Centrifugal force against the walls of the centrifuge tube created folds and creases in leaf tissue pressed, which then became nucleation points for necrosis. Therefore, for this small scale proof-of-concept experiment, each whole leaf was structurally reinforced by rolling it along the axis of its midrib in a strip of aluminum foil. The leaf was then inserted into a 50 mL FALCON™ tube, with each FALCON™ tube possessing 8-15 circular perforations about 3 mm in diameter each. The perforated tubes were then transported to a BECKMAN™ GS-6KR (BECKMAN COULTER™, Inc., Brea, Calif.) centrifuge in a humid box. Collection caps were fashioned from the bottom halves of 50 mL FALCON™ tubes and they were positioned in the centrifuge under the perforated tubes to catch the recovered AWF for each sample. The centrifuge was run at 25° C. for 15 minutes at 950 g, conditions that consistently dried all the leaves without causing them any visible damage throughout the experiment.

Homogenate Extraction

At 8 dpi, the midrib was excised from each leaf to separate the left side from the right (FIG. 9). Each side was homogenized with liquid nitrogen, and the resultant powder was resuspended in 10 mL/g FW of ice cold harvest buffer in a 15 mL FALCON™ tube. The powder was allowed to incubate in the tube in an ice bath for ten minutes prior to centrifugation for 10 min at 4° C. and 6,000 g. Exactly 1 mL of the supernatant was decanted into 1.5 mL EPPENDORF™ tubes and centrifuged again for 20 min at 4° C. and 20,000 g (Eppendorf Centrifuge 5403, Hauppauge, N.Y.) prior to assaying.

Quantitative Analysis

The activity of E1 endoglucanase was measured fluorometrically using methylumbelliferyl-β-D-cellobioside (MUC) as a substrate as described previously (Lindenmuth and McDonald 2011; Ziegelhoffer et al. 2001). E1 converts the MUC substrate, which is not fluorescent, to 4-methylumbelliferone (MU), and 3 µM MU diluted in acetate buffer (50 mM acetate, 100 mM NaCl, pH=5.5) was used to generate a standard curve. Samples were incubated in 700 µL of 1000 µM MUC dissolved in acetate buffer in 1.5 mL EPPENDORF™ tubes at 65° C. for 30 min. Transferred to triplicate wells containing 50 µL stop buffer (150 mM glycine buffer, pH=10.0) was 50 µL of this reaction volume at 0 min, 15 min, and 30 min. Change in fluorescence in black opaque 96-well plates (λex360 nm/λem460 nm) was measured with a SPECTRAMAX™ M2 (Molecular Devices, Sunnyvale, Calif.).

The total soluble protein assay was performed by the method of Bradford (Gregory 1966) using Coomassie Brilliant Blue G-250 dye (BIO-RAD™, Hercules, Calif.). A standard curve was produced from bovine serum albumin (BSA) (FISHER CHEMICAL™, Pittsburgh, Pa.) diluted in harvest buffer. Sample, diluted sample, or standard measuring 10 µL was added to 90 µL harvest buffer in a 96-well plate. Bradford dye measuring 200 µL was added to each well and color was developed for five minutes prior to the measurement of absorbance at 590 nm by a SPECTRAMAX™ 340pc.

Malate dehydrogenase activity assay for measurement of intracellular contamination in apoplast wash fluid or rinse fluid was performed as described (Terry and Bonner 1980; Ting 1968). A standard curve was produced from 0.75 mM β-nicotinamide adenine dinucleotide, reduced dipotassium salt (NADH) (SIGMA-ALDRICH™, St. Louis, Mo.) diluted in 50 mM phosphate buffer (pH=7.5), 200 µL per well. Then, 10 µL sample or diluted sample was added to 90 µL phosphate buffer in a 96-well plate at room temperature. The reaction was started when 50 µL 1.5 mM and 50 µL of 2 mM oxaloacetic acid (OAA) (SIGMA-ALDRICH™, St. Louis, Mo.) was added to each sample or diluted sample well. The decrease in absorbance at 340 nm in the sample wells, corresponding to the conversion of NADH to NAD+ by MDH in a reversible redox reaction that also converts OAA to malate, was monitored for three minutes and compared to the NADH standard curve by a SPECTRAMAX™ 340pc.

Immunohistochemistry

Leaf tissue was prepared for immunohistochemical imaging using established methods (Paciorek et al. 2006). Small 1 cm strips of leaf tissue were excised and fixed in 4% paraformaldehyde solution at 4° C. overnight. Using an autotechnicon, the strips were brought through ethanol and toluene gradients prior to embedding in paraffin wax blocks using a LEICA™ Histo-Embedder (LEICA™ Microsystems, Wetzlar, Germany). Sections 8 µm thick were mounted on poly-L-lysine coated slides and deparaffinized with xylene. With a in situ robot, InSitu Pro VSi (Intavis AG, Cologne, Germany) samples were tagged with 1:600 dilution of mouse monoclonal primary antibody against E1 (or a negative control without primary antibody) and then with a 1:500 dilution of goat anti-mouse ALEXA FLUOR™ 488 (Molecular Probes, Eugene, Oreg.). A LSM710 confocal microscope (CARL ZEISS™ Microscopy, LLC, Thornwood, N.Y.) with a LDC-apochromat 40X/1.1W Korr M27 water-emerged objective (n.a. 1.1) was used to capture images under 6% 488 nm laser excitation and 519-568 nm spectral detection for ALEXA FLUOR™ 488 or 640-750 nm for chloroplast auto-fluorescence by sequential channel detection. Captured images were manipulated for display by Zen 2011 (ZEISS™) and ImageJ (National Institutes of Health, Washington, D.C.) image analysis software packages.

Calculations

The percent yield of a component may be calculated by the formula:

$$\% \text{ yield} = 100\% * \frac{\sum_{i=1}^{n} AWF_i + \sum_{i=1}^{n} RF_i}{\text{total}} \quad (1)$$

where the "total" is the amount of the component in the leaf prior to recovery, assumed to be the sum of the yields from all the AWF, all the RF, and the WHE.

The purity fold improvement of a component calculated for a given sample (AWF, RF, or WHE) was calculated as the ratio of its specific yield relative to the specific yield in the total. The purity fold improvements in volume V of component k can be given as follows:

$$\text{Purity fold improvement} = \frac{[k]_v/[TSP]_v}{[k]_{total}/[TSP]_{total}} \quad (2)$$

Statistical analysis was performed using MICROSOFT™ Excel software. Standard deviations reported throughout this paper were calculated just from sample-to-sample variability as other possible sources of uncertainty such as assaying, volume or leaf weight measurements were considered negligible compared to this. Whether values were statistically different was determined using two-tailed paired student's t-tests using a 99% confidence interval as the threshold for significance.

Results

Daily Recovery of AWF

Without wishing to be bound by theory, it was imagined that repeated rounds of AWF recovery throughout the production phase in agroinfiltrated *Nicotiana benthamiana* leaves may allow for recovery of higher apoplast protein yields. If the vacuum infiltration and centrifugation forces were mild enough, the leaf tissue would be largely unaffected by the process. Meanwhile, the apoplast would be mostly evacuated, perhaps improving the kinetics for secretion, and the secreted recombinant protein would be vastly more stable outside of the leaf in the AWF, where conditions were designed for optimal stability.

Figure 10:
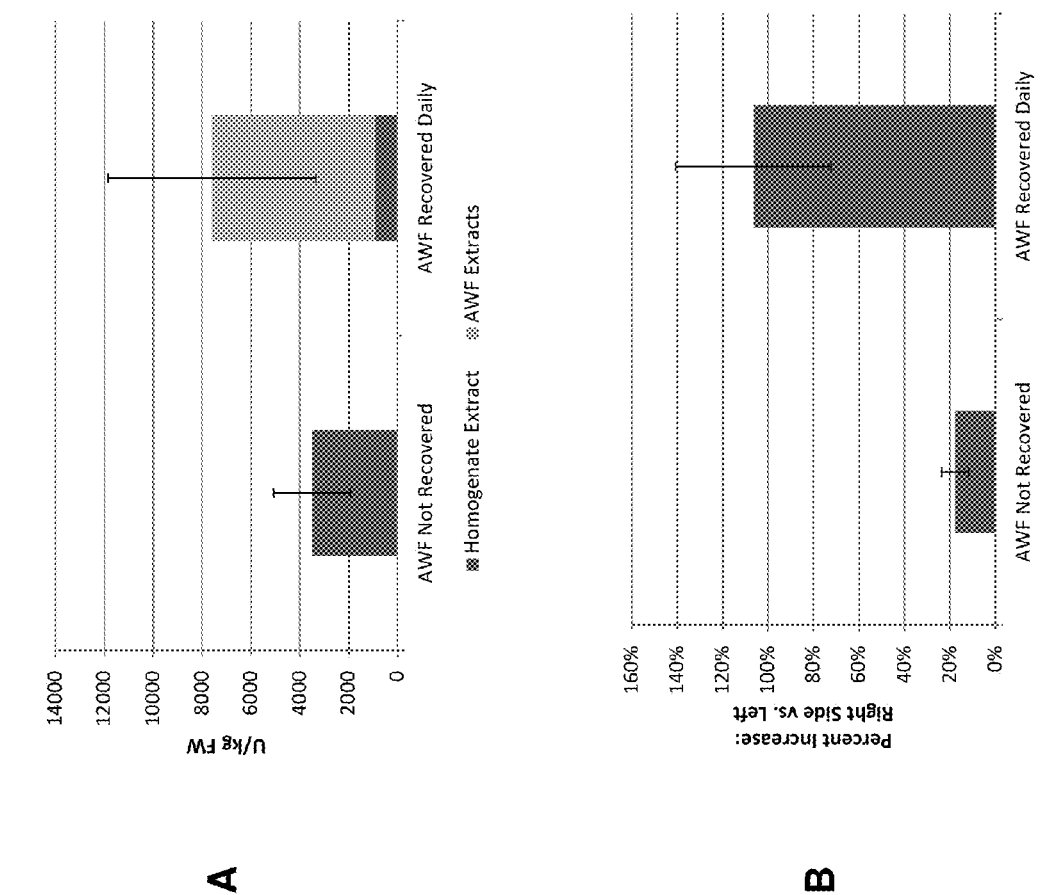
FIG. 10A illustrates a comparison of overall transient expression of units of E1cd activity per kilogram fresh weight from leaf tissue with or without daily AWF recovery during incubation. Shown are the yields from the homogenate extract and, in the case of the AWF recovered daily tissue, the yield as well from the AWF fluid pooled from six days of collection (n=3).
FIG. 10B illustrates the percent increase in expression level of the right side over the leaf side of leaves for leaves with or without AWF recovered daily. For AWF recovered daily leaves, only the right side was buffer infiltrated prior to centrifugation whereas for AWF not recovered leaves, neither side was either buffer infiltrated or centrifuged (n=3; statistical significance=99.5%).

The total E1 endoglucanase activity expressed in tissue with AWF recovered daily was higher than that in tissue from which AWF was never recovered. Expression was 2.2-fold greater with AWF recovered daily than with AWF never recovered, 7600 vs. 3500 U/kg FW on average (Table 3). Furthermore, with AWF recovered daily, on average 84% of the E1cd activity was recovered in AWF samples while only 16% was left behind in the residual tissue. Since daily AWF recovery was so effective at removing E1cd from the leaf tissue and since the method more than doubled expression levels, the yields from pooled AWF alone surpassed by on average 75% the yields from extraction by the conventional method of unperturbed incubation followed by homogenization at 8 dpi (FIG. 10A).

TABLE 3

E1cd expression levels (U/kg FW) in homogenate extract and pooled AWF samples

| | Leaf side | Right side | | | |
|---|---|---|---|---|---|
| | HE | HE | AWF | Total | RS vs. LS |
| AWF Recovered Daily | | | | | |
| Leaf 1 | 4794 | 957 | 10404 | 11361 | 137% |
| Leaf 2 | 3958 | 836 | 7592 | 8427 | 113% |
| Leaf 3 | 1755 | 920 | 2053 | 2973 | 69% |
| Average | 3502 | 904 | 6683 | 7587 | 106% |
| AWF Not Recovered | | | | | |
| Leaf 1 | 6929 | 8081 | NC | 8081 | 17% |
| Leaf 2 | 3834 | 4757 | NC | 4757 | 24% |
| Leaf 3 | 2421 | 2720 | NC | 2720 | 12% |
| Average | 4395 | 5186 | — | 5186 | 18% |

While values for yield per mass of leaf tissue were highly variable from leaf-to-leaf, comparing samples from the same leaf with or without AWF daily recovery showed a significant trend. From every leaf tested, yields improved 106%±34% where AWF was recovered daily compared to where it was not, which in this experiment was the right side of the leaf and the left side, respectively (abaxial side face up; FIG. 9). As a control, triplicate leaves incubating unperturbed during E1cd expression exhibited 18%±6% greater expression on the right side than the left, a value that is not negligible but still nonetheless most likely coincidental (a supposition supported by how there was no such difference observed interpreting the data for TSP or MDH content, data not shown). The two data were significantly different, with confidence interval of 99.6%, firmly demonstrating that daily AWF recovery was responsible for enhanced E1cd yields (FIG. 10B).

Figure 11:
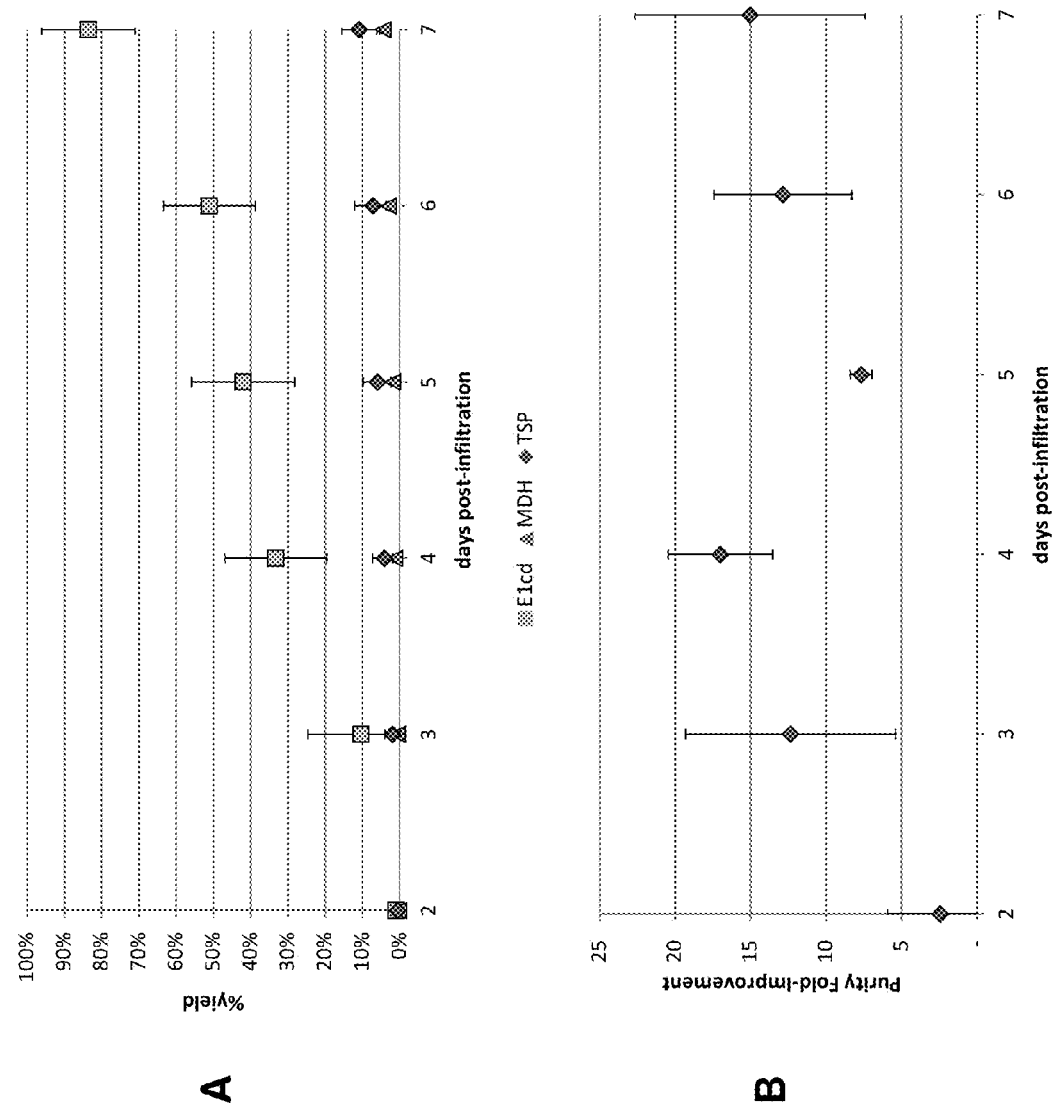
FIG. 11A illustrates that in leaf tissue with AWF recovered daily transiently expressing E1cd, the percent yields of E1cd activity, malate dehydrogenase (MDH) activity, and total soluble protein (TSP) accumulated in AWF after its recovery each day, reported as a percent of each sample's overall expression level (n=3).
FIG. 11B illustrates the relative purity-fold improvement of E1cd as a % TSP in each day's recovered AWF compared to overall E1cd % TSP for each tissue sample.

The percent yield of E1cd in AWF (84%) was substantially more than for TSP (10%) or the intracellular marker malate dehydrogenase (MDH; 4%) (See FIG. 11A), demonstrating that apoplast washing in this experiment selectively recovered secreted proteins and protected cellular integrity. The effect is that AWF samples had dramatically greater purity as a percent of total soluble protein compared to a homogenate extracted from regions of the leaf where AWF never recovered (FIG. 11B). The composition of each day's AWF was individually assayed, and it was found that the most E1cd was recovered on days 4 and 7 post-incubation. The E1cd purity was highest at 4 dpi, suggesting that this was the day when E1cd production was at its peak. Meanwhile, even though there was a big increase in the amount of E1cd recovered between 6 dpi and 7 dpi, there was no corresponding increase in purity, suggesting that the boost in recovery on this day was related instead to a change in extracellular matrix morphology.

Other physical changes in the tissue observed at 7 dpi included weight loss, less resistance to buffer infiltration in the vacuum chamber, and less force and time required to recover AWF in the centrifuge, traits that were followed the next day by signs of necrosis, such as black spots or translucency. Therefore, it should be noted that the tissue possessed traits desirable for bulk AWF recovery at the later stages of this experiment. Meanwhile, the control leaves with AWF never recovered also started to necrotize at 8 dpi, so the procedure itself was deemed to have a neutral effect on leaf health as long as the forces driving fluid into and out of the leaf were controlled to be as gentle as possible.

It was also observed that the E1cd in residual HE with AWF daily recovery was remarkably consistent, perhaps indicating that there is a saturation level for the extracellular matrix above which overflow secreted proteins might be more freely accessible to apoplast washing. Without wishing to be bound by theory, tissues with higher overall yields of recombinant protein should release increasingly higher percent yields into AWF, as was the basic trend in this experiment. Higher expressing leaves also saw the greatest increase in their expression levels in regions where AWF was recovered daily.

Confocal Microscopy

Figure 12:
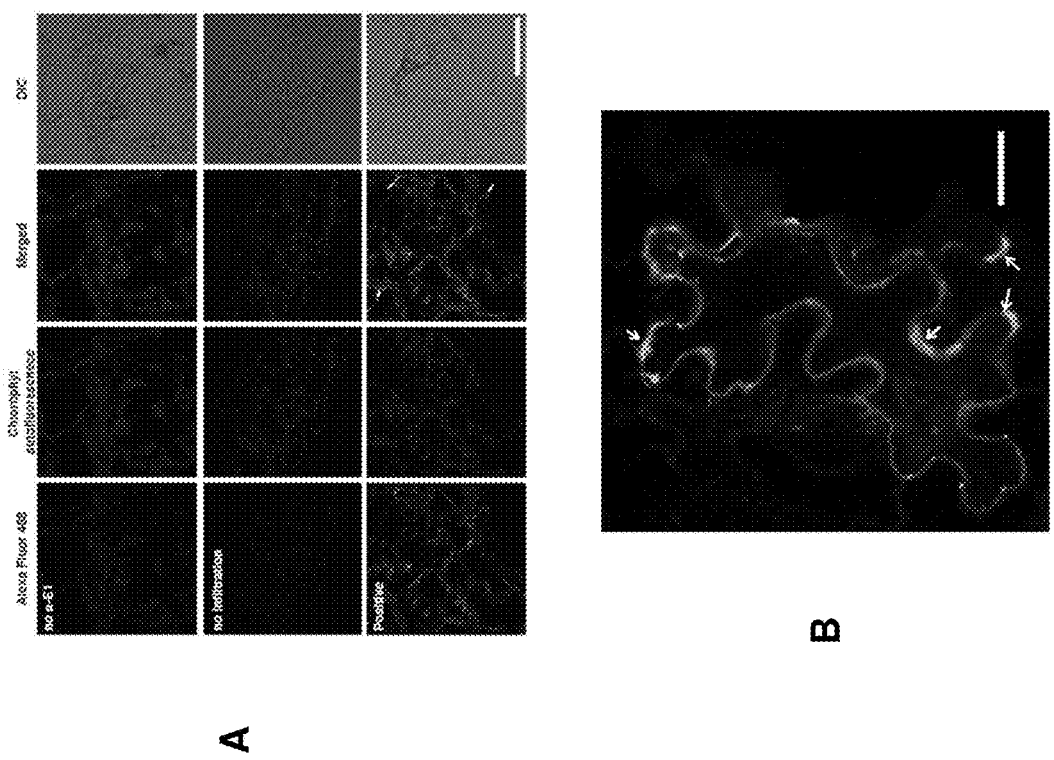
FIG. 12A illustrates fluorescent confocal immunohistochemical images of *N. benthamiana* mesophyll cross-sections. Top) Negative control without E1cd primary antibody on E1cd expressing tissue. Middle) Negative control with antibodies but on tissue not agroinfiltrated with the E1cd vector. Bottom) Positive sample expressing E1cd activity.
FIG. 12B illustrates an image of E1cd expressing epidermal tissue. Arrows indicate regions of strongest signal. Scale bar=20 μm.

An immunohistochemistry experiment with *N. benthamiana* tissue transiently expressing E1cd was performed to confirm that the recombinant protein was successfully secreted to the apoplast, explaining its selective recovery by VI-C. Mesophyll cross-sections were imaged (FIG. 12A) as was the epidermal layer (FIG. 12B). The fluorescent signal from the antibodies targeting E1cd was strongest in between cells or along their periphery. The localization of the signal was most clear in the epidermal layer, but it is imagined that apoplast washing is most effective among the more loosely-packed cells in the mesophyll layer. Furthermore, the signal was not present in negative control samples either without E1cd expression or without the primary antibody. Therefore, it can be concluded from the imaging experiment that it was specific for targeting the localization of E1cd and also that E1cd was secreted into the apoplast.

CONCLUSIONS

By taking *N. benthamiana* tissue expressing a secreted recombinant protein and recovering that protein daily by a non-destructive vacuum infiltration-centrifugation method, not only was that protein recovered at improved concentration and purity over conventional homogenization methods, but the overall amount of that protein produced by the leaf tissue more than doubled. These results therefore offer a new dimension to how expression levels in agroinfiltrated leaves might be enhanced.

REFERENCES

T. J. Menkhaus, Y. Bai, C. M. Zhang, Z. L. Nikolov, C. E. Glatz, Considerations for the recovery of recombinant proteins from plants, Biotechnology Progress, 20 (2004) 1001-1014.

S. Hassan, c. J. van Dolleweerd, F. loakeimidis, E. Keshavarz-Moore, J. K. C. Ma, Considerations for extraction of monoclonal antibodies targeted to different subcellular compartments in transgenic tobacco plants, Plant Biotechnology Journal, 6 (2008) 733-748.

L. R. Wilken, Z. L. Nikolov, Recovery and purification of plant-made recombinant proteins, Biotechnology Advances, 30 (2012) 419-433.

Z. Klement, METHOD OF OBTAINING FLUID FROM INTERCELLULAR SPACES OF FOLIAGE AND FLUIDS MERIT AS SUBSTRATE FOR PHYTOBACTERIAL PATHOGENS, Phytopathology, 55 (1965) 1033-&.

W. G. Rathmell, L. Sequeira, SOLUBLE PEROXIDASE IN FLUID FROM INTERCELLULAR SPACES OF TOBACCO-LEAVES, Plant Physiology, 53 (1974) 317-318.

Turpen T H, Garger S J, McCulloch M J, Cameron T I, Samonek-Potter M L, Holtz R B; Large Scale Biology Corporation, assignee. 2006 Apr. 25, 2006. Method for Recovering Proteins from the Interstitial Fluid of Plant Tissues. U.S. Pat. No. 7,034,128.

R. Lombardi, M. E. Villani, M. Di Carli, P. Brunetti, E. Benvenuto, M. Donini, Optimisation of the purification process of a tumour-targeting antibody produced in *N. benthamiana* using vacuum agroinfiltration, Transgenic Research, 19 (2010) 1083-1097.

V. K. Hehle, M. J. Paul, P. M. Drake, J. K. C. Ma, C. J. Van Dolleweerd, Antibody degradation in tobacco plants: a predominantly apoplastic process, in: BMC Biotechnology, 2011.

P. M. Doran, Foreign protein degradation and instability in plants and plant tissue cultures, Trends in Biotechnology, 24 (2006) 426-432.

D. D. Kuta, L. Tripathi, *Agrobacterium*-induced hypersensitive necrotic reaction in plant cells: a resistance response against *Agrobacterium*-mediated DNA transfer, African Journal of Biotechnology, 4 (2005) 752-757.

E. James, D. R. Mills, J. M. Lee, Increased production and recovery of secreted foreign proteins from plant cell cultures using an affinity chromatography bioreactor, Biochemical Engineering Journal, 12 (2002) 205-213.

T. Ziegelhoffer, J. A. Raasch, S. Austin-Phillips, Dramatic effects of truncation and sub-cellular targeting on the accumulation of recombinant microbial cellulase in tobacco, Molecular Breeding, 8 (2001) 147-158.

Conrad U, Fiedler U. 1998. Compartment-specific accumulation of recombinant immunoglobulins in plant cells: an essential tool for antibody production and immunomodulation of physiological functions and pathogen activity. Plant Molecular Biology 38(1-2):101-109.

Delannoy M, Alves G, Vertommen D, Ma J, Boutry M, Navarre C. 2008. Identification of peptidases in *Nicotiana tabacum* leaf intercellular fluid. Proteomics 8(11):2285-2298.

Geldner N. 2004. The plant endosomal system—its structure and role in signal transduction and plant development. Planta 219(4):547-560.

Gregory R P F. 1966. A rapid assay for peroxidase activity. Biochemical Journal 101(3):582-&.

Hegde R S, Bernstein H D. 2006. The surprising complexity of signal sequences. Trends in Biochemical Sciences 31(10):563-571.

Hellwig S, Drossard J, Twyman R M, Fischer R. 2004. Plant cell cultures for the production of recombinant proteins. Nature Biotechnology 22(11):1415-1422.

Lindenmuth B E, McDonald K A. 2011. Production and characterization of *Acidothermus cellulolyticus* endoglucanase in *Pichia pastoris*. Protein Expression and Purification 77(2):153-158.

Lohaus G, Pennewiss K, Sattelmacher B, Hussmann M, Muehling K H. 2001. Is the infiltration-centrifugation technique appropriate for the isolation of apoplastic fluid? A critical evaluation with different plant species. Physiologia Plantarum 111(4):457-465.

Nakamura Y, Gojobori T, Ikemura T. 2000. Codon usage tabulated from international DNA sequence databases: status for the year 2000. Nucleic Acids Research 28(1):292-292.

Nausch H, Mischofsky H, Koslowski R, Meyer U, Broer I, Huckauf J. 2012. Expression and Subcellular Targeting of Human Complement Factor C5a in *Nicotiana* species. Plos One 7(12).

Paciorek T, Sauer M, Balla J, Wisniewska J, Friml J. 2006. Immunocytochemical technique for protein localization in sections of plant tissues. Nature Protocols 1(1):104-107.

Rathmell W G, Sequeira L. 1974. Soluble peroxidase in fluid from intercellular spaces of tobacco leaves. Plant Physiology 53(2):317-318.

Sharp J M, Doran P M. 2001. Strategies for enhancing monoclonal antibody accumulation in plant cell and organ cultures. Biotechnology Progress 17(6):979-992.

Smith J M, Van Ness H C, Abbott M M. 2005. Vapor/Liquid Equilibrium: Introduction. Introduction to Chemical Engineering Thermodynamics. Singapore: McGraw Hill. p 338-370.

Surpin M, Raikhel N. 2004. Traffic jams affect plant development and signal transduction. Nature Reviews Molecular Cell Biology 5(2):100-109.

Terry M E, Bonner B A. 1980. An examination of centrifugation as a method of extracting an extracellular solution from peas, and its use for the stud of indoleacetic acid-induced growth. Plant Physiology 66(2):321-325.

Ting I P. 1968. Malic Dehydrogenases in Corn Root Tips. Archives of Biochemistry and Biophysics 126(1):1-&.

Trudel J, Potvin C, Asselin A. 1995. Secreted hen lysozyme in transgenic tobacco—recovery of bound enzyme and in-vitro growth inhibitions of plant-pathogens. Plant Science 106(1):55-62.

USDA A, National Genetic Resources Program. 2012. PI 555478 *Nicotiana benthamiana* Domin Solanaceae. 1962 ed.

What is claimed is:

1. A method of extracting a recombinant protein in an excised tobacco leaf tissue, the method comprising:
   providing an excised tobacco leaf tissue comprising a nucleic acid encoding a recombinant protein in operable combination with a promoter;
   incubating the tobacco leaf tissue under suitable conditions such that the recombinant protein is expressed and located to an apoplast of a plant cell of the tobacco leaf tissue;
   contacting the tobacco leaf tissue with a rinse fluid on a plurality of occasions over the course of a production interval to release the recombinant protein from the apoplast into the rinse fluid to create an apoplast wash fluid, wherein the production interval begins about on the second day after initiation of the incubation and the production interval ends about on the sixth day after initiation of the incubation, and wherein each occasion of the plurality of occasions occurs about once every 24 hours over the course of the production interval;
   wherein content of the recombinant protein in the apoplast wash fluid from tobacco leaf tissue contacted with rinse fluid on a plurality of occasions is higher than the content of the recombinant protein in the apoplast wash fluid from comparable tobacco leaf tissue contacted with rinse fluid only at the end of the production interval, and wherein at least a portion of the tobacco leaf tissue remains viable for expression of the recombinant protein after each occasion of the plurality of occasions.

2. The method of claim 1, wherein the recombinant protein is a cellulase.

3. The method of claim 2, wherein the cellulase is E1 endoglucanase.

4. The method of claim 1, wherein the promoter is a CaMV 35S promoter.

5. The method of claim 1, wherein the contacting step comprises vacuum-infiltrating the tobacco leaf tissue to produce a vacuum-infiltrated tobacco leaf tissue submerged in the rinse fluid.

6. The method of claim 5, further comprising centrifuging the vacuum-infiltrated tobacco leaf tissue to facilitate separation of the apoplast wash fluid from the tobacco leaf tissue.

7. The method of claim 6, wherein force of the centrifuging step is not more than 30 kPa.

8. The method of claim 7, wherein centrifugation occurs for not more than 20 minutes.

9. The method of claim 1, wherein the rinse fluid comprises a protein-stabilization agent.

10. The method of claim 1, wherein content of the recombinant protein in the apoplast wash fluid from tobacco leaf tissue contacted with rinse fluid on a plurality of occasions is at least two-fold higher than the content of the recombinant protein in the apoplast wash fluid from comparable tobacco leaf tissue contacted with rinse fluid only at the end of the production interval.

11. The method of claim 1, further comprising recovering the recombinant protein from the apoplast wash fluid.

* * * * *